US011410776B1

(12) United States Patent
Rahman et al.

(10) Patent No.: US 11,410,776 B1
(45) Date of Patent: Aug. 9, 2022

(54) SYSTEMS AND METHODS FOR FORMAL THREAT ANALYSIS OF A SMART HEALTHCARE SYSTEM

(71) Applicants: Mohammad Ashiqur Rahman, Miami, FL (US); Nur Imtiazul Haque, Miami, FL (US)

(72) Inventors: Mohammad Ashiqur Rahman, Miami, FL (US); Nur Imtiazul Haque, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/653,520

(22) Filed: Mar. 4, 2022

(51) Int. Cl.
*G16H 50/20* (2018.01)

(52) U.S. Cl.
CPC .................................. *G16H 50/20* (2018.01)

(58) Field of Classification Search
CPC ....................................................... G16H 50/20
USPC ............................................................. 705/2
See application file for complete search history.

(56) References Cited

U.S. PATENT DOCUMENTS

2012/0242501 A1* 9/2012 Tran ..................... A61B 5/4875
340/870.02

* cited by examiner

*Primary Examiner* — Michael Tomaszewski
*Assistant Examiner* — Rachael Sojin Stone
(74) *Attorney, Agent, or Firm* — Saliwanchik, Lloyd & Eisenschenk

(57) ABSTRACT

Systems and methods for formal threat analysis of smart healthcare systems (SHSs) are provided. The system can formally analyze supervised and unsupervised machine learning models for black-box-style SHS threat analysis. The system can analyze the underlying decision-making model of SHSs by investigating the possible attacks that can be deployed by minimal alteration of sensor values.

20 Claims, 29 Drawing Sheets

| Vital Signs | Model | Feature Parameter Value | Database |
|---|---|---|---|
| Heart Rate | KardiaMobile 6L | 60-100 beats per minute | Fetal ECG Synthetic Database, Data.Gov |
| Blood Pressure | Greater Goods | Systolic (120 mm Hg) and Diastolic (80 mm Hg) | Fetal ECG Synthetic Database, Data.Gov |
| Blood Glucose | Dario | 70-130 mg/dl | UCI ML database of diabetes |
| Blood Oxygen | iHealth Air Wireless Pulse Oximeter | Oxygen Saturation level ≥ 94% | Pattern Analysis of Oxygen Saturation Variability |
| Respiratory Rate | QuardioCore | 12-20 Breaths per minute | BIDMC PPG and Respiration Dataset |
| Blood Alcohol | Scram Continuous Alcohol Monitoring (Cam) | 0.08 g/dl | StatCrunch dataset |

FIG. 14

| Model Type | ML Model | Symbol | Description | Type |
|---|---|---|---|---|
| All | All | $n_s$ | Number of sensors | Integer |
| | | $n_l$ | Number of labels | Integer |
| | | $a, b$ | Sensors | String |
| | | $j$ | Patient's status | String |
| | | $S$ | Set of all sensors | Set |
| | | $Z$ | Set of all possible statuses for a patient | Set |
| | Decision Tree | $N_f^f$ | Set of all nodes in path $f$ | Set |
| | | $N_P$ | Set of all nodes | Set |
| | | $P_{th}$ | Set of all paths from root to leaf | Set |
| | Logistic Regression | $\theta_{gi}$ | Model parameter (weight) for $i$-th sensor and $g$-th patient status | Real |
| | | $\theta_g$ | Set of model parameter (weight) for $g$-th patient status | Set |
| | | $\theta$ | Set of all model parameter (weight) | Set |
| | | $intercept_g$ | Model parameter (bias) for $g$-th patient status | Real |
| | | $intercept$ | Set of all model parameter (bias) | Set |
| | Neural Network | $NL_i$ | Set of Nodes in $i$-th layer | Set |
| | | $NL$ | Sets of all layers | Sets |
| Disease Classification Model | | | | |
| Anomaly Detection Model | DBScan, K-means | $C_k^{a,b,j}$ | $k$-th cluster for the sensor pair $(a, b)$ for a patient with status, $j$ | Cluster |
| | | $Cls^{a,b,j}$ | Set of all clusters for the sensor pair $(a, b)$ for a patient with status, $j$ | Set |
| | | $Ls_i^{a,b,j}$ | $i$-th line segment of the clusters for the sensor pair $(a, b)$ and the patient's status, $j$ | Tuple |
| | | $Ls^{a,b,j}$ | Set of all line segments of the clusters for the sensor pair $(a, b)$ and the patient's status, $j$ | Set |
| | | $Cel$ | Sets of all clusters | Sets |
| | | $Ls_{all}$ | Sets of all line segments | Sets |

FIG. 15

|  | Heart Rate | Systolic | Diastolic | Blood Oxygen |
|---|---|---|---|---|
| Actual measurements | 122.94 | 75.98 | 153.56 | 93.2 |
| Attacked measurements (DT constraints only) | 122.94 | 73.46 | 153.56 | 98.5 |
| Attacked measurements (both DT and DBScan constraints) | 120.332 | 81.855 | 149.67 | 98.5 |

FIG. 16

$inference(\mathcal{P}, 0) \rightarrow (((\mathcal{P}_5 \leq 20.5) \wedge (((\mathcal{P}_7 \leq 8.5) \wedge (\mathcal{P}_4 \leq 94.005))$
$\vee ((\mathcal{P}_7 \leq 8.5) \wedge (\mathcal{P}_2 \leq 140.46) \wedge (\mathcal{P}_0 \leq 100.51)))) \vee$
$((\mathcal{P}_5 > 20.5) \wedge (\mathcal{P}_3 > 130.495)))$ $inference(\mathcal{P}, 1) \rightarrow (((\mathcal{P}_3 > 20.5) \wedge (\mathcal{P}_3 \leq 130.495) \wedge (\mathcal{P}_2 \leq 140.46))$ $inference(\mathcal{P}, 2) \rightarrow (((\mathcal{P}_3 > 20.5) \wedge (\mathcal{P}_3 \leq 130.495) \wedge (\mathcal{P}_2 > 140.46))$ $inference(\mathcal{P}, 3) \rightarrow (\mathcal{P}_5 \leq 20.5) \wedge (\mathcal{P}_7 > 8.5) \wedge (\mathcal{P}_5 \leq 20.5)$ $inference(\mathcal{P}, 4) \rightarrow (\mathcal{P}_5 \leq 20.5) \wedge (\mathcal{P}_7 \leq 8.5) \wedge (\mathcal{P}_4 > 94.005) \wedge$
$(\mathcal{P}_2 \leq 140.46)) \wedge (\mathcal{P}_0 > 100.51)$ $inference(\mathcal{P}, 5) \rightarrow (\mathcal{P}_5 \leq 20.5) \wedge (\mathcal{P}_7 \leq 8.5) \wedge (\mathcal{P}_4 > 94.005) \wedge$
$(\mathcal{P}_2 > 140.46)$

FIG. 17

$$...((((-0.75\mathcal{P}_0^0 + 0.35\mathcal{P}_1^0 + 79.029 \geq 0) \wedge (70.11 \leq \mathcal{P}_1^0 \leq 70.86)) \oplus$$
$$((-1.5\mathcal{P}_0^0 + 0.53\mathcal{P}_1^0 + 171.7767 \geq 0) \wedge (68.61 \leq \mathcal{P}_1^0 \leq 70.11)) \oplus$$
$$((-0.08\mathcal{P}_0^0 + 0.53\mathcal{P}_1^0 + 171.7767 \geq 0) \wedge (65.21 \leq \mathcal{P}_1^0 \leq 67.44)) \vee$$
$$(((0.08\mathcal{P}_0^0 + 0.39\mathcal{P}_1^0 + 1059.126 \geq 0) \wedge (85.27 \leq \mathcal{P}_1^0 \leq 87.36)) \oplus ((0.04\mathcal{P}_0^0 +$$
$$0.43\mathcal{P}_1^0 + 21.929 \geq 0) \wedge (88.22 \leq \mathcal{P}_1^0 \leq 92.33)) \oplus ((0.04\mathcal{P}_0^0 + 0.41\mathcal{P}_1^0 +$$
$$21.21 \geq 0) \wedge (87.35 \leq \mathcal{P}_1^0 \leq 91.15)))$$

FIG. 18

|  |  | NN | DT | LR |
|---|---|---|---|---|
| Synthetic Data | Accuracy | 0.91 | 0.93 | 0.88 |
|  | Precision | 0.92 | 0.92 | 0.9 |
|  | Recall | 0.89 | 0.93 | 0.9 |
|  | F1-Score | 0.9 | 0.92 | 0.9 |
| UQVS Data | Accuracy | 0.94 | 0.97 | 0.86 |
|  | Precision | 0.9 | 0.92 | 0.88 |
|  | Recall | 0.91 | 0.92 | 0.86 |
|  | F1-Score | 0.9 | 0.92 | 0.87 |

FIG. 19

| | Synthetic Data | | | | UQVS Data | | | |
|---|---|---|---|---|---|---|---|---|
| | DBS | SCS | DI | DBS | | SCS | DI | |
| K-means | 2.57 | 0.18 | 0.057 | 1.841 | | 0.098 | 0.072 | |
| DBSCAN | 0.681 | 0.732 | 0.235 | 0.517 | | 0.612 | 0.412 | |

FIG. 20

| Model | Synthetic Dataset | | UQVS Dataset | |
|---|---|---|---|---|
| | Positive Sample | Noisy Sample | Positive Sample | Noisy Sample |
| All measurements consideration | 13822 | 3178 | 182,316 | 26,799 |
| Combination of pair of measurements consideration | 13967 | 3033 | 183,215 | 25,900 |

FIG. 21

| Current State | Target State | Number of Sensors to Compromise | Sensors |
|---|---|---|---|
| Normal | High Cholesterol | 3 | Heart rate, Glucose, Alcohol |
| High Blood Pressure | Abnormal Oxygen Level | 4 | Systolic, Diastolic, Oxygen, Breathing |
| High Cholesterol | Excessive Sweating | 2 | Heart rate, Breathing |

FIG. 22

| Dataset | # Measurements | Number of Clauses | | |
|---|---|---|---|---|
| | | NN | DT | LR |
| Synthetic Data | 8 | 2652 | 5196 | 2148 |
| | 10 | 2694 | 5104 | 2160 |
| | 12 | 2736 | 5349 | 2172 |
| | 14 | 2778 | 5465 | 2184 |
| | 16 | 2820 | 897 | 2196 |
| UQVS Data | 26 | 178962 | 56813 | 172608 |
| | 27 | 179005 | 56689 | 172666 |
| | 28 | 179048 | 57071 | 172724 |
| | 29 | 179091 | 57094 | 172782 |
| | 30 | 179134 | 59124 | 172840 |

FIG. 23

SYSTEMS AND METHODS FOR FORMAL THREAT ANALYSIS OF A SMART HEALTHCARE SYSTEM

BACKGROUND

Traditional healthcare systems rely heavily on hospitalization, specialized consultation, and nursing that require a lot of human intervention. These can introduce delayed or incorrect treatment, resulting in increased treatment cost or human mortality. In the United States, the aggregated patient treatment cost was almost $3.81 trillion in 2019, which is projected to be even higher as time goes on, for example, due to COVID-19. An automated healthcare system could reduce this cost and the death rate. Contemporary internet of medical things (IoMT) technology has brought a radical revolution in the healthcare domain by enhancing the reliability of remote patient monitoring, increasing efficiency of the medical sensors, and eliminating latency between disease detection and medication.

The smart healthcare system (SHS) is a modern cyber-physical system (CPS) that continuously collects data from the IoMT sensor network connected to the human body, processes them accordingly for making required control decisions, and triggers implantable medical devices (IMDs) for real-time medication and treatment. Currently, healthcare facilities are more efficient, accessible, and personalized as the SHS is ameliorating disease diagnostic tools, treatment for patients, and healthcare devices, thus improving the quality of life. However, an SHS requires processing a lot of historical data to identify anomalous sensor measurements. The data related to healthcare and medication are affluent. They can be utilized to reveal intricate patterns of dependency between various vital signs of the human body for accurate and precise disease classification. In order to achieve faster processing, an SHS integrates the concept of IoMT with big data, cloud computing, and artificial intelligence.

With the advent of SHSs, smart medical devices are exposed to numerous attack points and are susceptible to potential threats. Cyberattacks on the healthcare industry are rapidly growing, and SHS devices and IMDs often have vulnerabilities that expose significant threats. A majority of the healthcare organizations were attacked between October 2018 and October 2019 (Ponemon Institute. 2019 Global State of Cybersecurity in Small and Medium-Sized Businesses, October 2019, keeper.io/hubfs/PDF/ 2019%20Keeper %20Report %20V7.pdf). Most popular cyberattacks in the healthcare system includes hardware Trojan, malware (e.g., Medjack), Sybil attacks using either hijacked IoMT or single malicious node, denial of service (DoS) attacks, or man-in-the-middle (MITM) attacks. At least 20% of medical device manufacturers experienced ransomware or malware attacks over a period of 20 months (Cybersecurity Insiders Naveen Goud. Malware and ransomware attack on Medical Devices, Last Accessed October 2020, cybersecurity-insiders.com/malware-and-ransomware-attack-on-medical-devices/).

BRIEF SUMMARY

In view of the aforementioned challenges, it is imperative to be aware of the vulnerabilities of a smart healthcare system (SHS) before deploying it. Embodiments of the subject invention provide novel and advantageous formal threat analysis systems (or analyzers) for SHSs, as well as methods of using the same. The analysis system can formally analyze supervised and unsupervised machine learning (ML) models for black-box-style SHS threat analysis. The system can analyze the underlying decision-making model of SHSs by investigating the possible attacks that can be deployed by minimal alteration of sensor values. Failures in safety-critical cyber-physical systems (CPSs), such as SHSs, can increase the possibility of life-threatening events. In order to increase reliability, SHSs often employ data validation or anomaly detection systems. Hence, the threat analysis system can consider a clustering-based anomaly detection model (ADM) in the SHS due to its real-time detection capability. The ADM can learn the pattern of sensor measurement relationships by analyzing massive data. The system can assess potential attack vectors of an SHS that uses ML algorithms, such as decision tree (DT), logistic regression (LR), and/or artificial neural network (ANN) for classifying diseases, as well as K-means and/or density-based spatial clustering of applications with noise (DBSCAN) clustering algorithms for detecting anomalies. The system can focus on quantifying the associated threat that can be performed by minor alteration in one or more sensor measurements of an SHS.

In an embodiment, 1. a system/framework for formal threat analysis of an SHS (that comprises an SHS database and at least one sensor collecting sensor data from at least one patient) can comprise: a processor; and a (non-transitory) machine-readable medium in operable communication with the processor and the SHS database, and having instructions stored thereon that, when executed by the processor, perform the following steps: i) training a disease classification model (DCM) using the SHS database to generate DCM output data comprising at least one label for the at least one patient; ii) training an ADM using the SHS database to check consistency of the sensor data and to generate ADM output data; iii) running an SHS decision control model, using the DCM output data and the ADM output data as input to the SHS decision control model, to generate SHS constraints; iv) generating attack constraints based on a capability of a potential attacker and a goal of the potential attacker; and v) running a satisfiability modulo theory (SMT) solver, using the SHS constraints, the attack constraints, and the sensor data as input to the SMT solver, to determine whether the goal of the potential attacker can be attained. The instructions when executed can further perform the following steps: vi) if the goal of the potential attacker can be attained, generating an attack vector and reporting the attack vector to a user of the system; and vii) if the goal of the potential attacker cannot be attained, increasing the capability of the potential attacker and running steps iv), v), vi), and vii) again. The system can further comprise a display in operable communication with the machine-readable medium, and the reporting of the attack vector can comprise displaying the attack vector on the display. The at least one sensor can comprise a plurality of sensors, and the increasing the capability of the potential attacker can comprise giving the potential attacker access to at least one additional sensor than the potential attacker had access to when step iv) was most recently performed. The SMT solver can first encode the SHS constraints, the attack constraints, and the sensor data as a constraint satisfaction problem (CSP), where the SMT solver can return a result of satisfactory for the CSP if the goal of the potential attacker can be attained and the SMT solver can return a result of unsatisfactory for the CSP if the goal of the potential attacker cannot be attained. Step vi) can further comprise, after generating the attack vector and reporting the attack vector, updating the goal of the potential attacker and running steps iv), v), vi), and vii) again. The process can be stopped once the respective attack vector has been generated and reported for all goals of a predetermined number of goals of the potential attacker (i.e., the goals for all types of attacks for which the user wants to analyze the threat to the SHS). The DCM can be, or can be trained using, a DT algorithm, an LR algorithm, or a neural network algorithm (e.g., an artificial neural network algorithm). The ADM can be, or can use, an unsupervised technique such as a DBSCAN algorithm or a k-means algorithm. For example, the DCM can be (or can be trained using) a DT algorithm and the ADM can be (or can use) a DBSCAN algorithm.

In another embodiment, a method for formal threat analysis of an SHS (that comprises an SHS database and at least one sensor collecting sensor data from at least one patient) can comprise: i) training (e.g., by a processor in operable communication with the SHS database and/or the at least one sensor) a DCM using the SHS database to generate DCM output data comprising at least one label for the at least one patient; ii) training (e.g., by the processor) an ADM using the SHS database to check consistency of the sensor data and to generate ADM output data; iii) running (e.g., by the processor) an SHS decision control model, using the DCM output data and the ADM output data as input to the SHS decision control model, to generate SHS constraints; iv) generating (e.g., by the processor) attack constraints based on a capability of a potential attacker and a goal of the potential attacker; and v) running (e.g., by the processor) an SMT solver, using the SHS constraints, the attack constraints, and the sensor data as input to the SMT solver, to determine whether the goal of the potential attacker can be attained. The method can further comprise: vi) if the goal of the potential attacker can be attained, generating (e.g., by the processor) an attack vector and reporting the attack vector to a user of the system; and vii) if the goal of the potential attacker cannot be attained, increasing (e.g., by the processor) the capability of the potential attacker and running steps iv), v), vi), and vii) again. The reporting of the attack vector can comprise displaying the attack vector (e.g., on a display in operable communication with the processor). The at least one sensor can comprise a plurality of sensors, and the increasing the capability of the potential attacker can comprise giving the potential attacker access to at least one additional sensor than the potential attacker had access to when step iv) was most recently performed. The SMT solver can first encode the SHS constraints, the attack constraints, and the sensor data as a CSP, where the SMT solver can return a result of satisfactory for the CSP if the goal of the potential attacker can be attained and the SMT solver can return a result of unsatisfactory for the CSP if the goal of the potential attacker cannot be attained. Step vi) can further comprise, after generating the attack vector and reporting the attack vector, updating the goal of the potential attacker and running steps iv), v), vi), and vii) again. The process can be stopped once the respective attack vector has been generated and reported for all goals of a predetermined number of goals of the potential attacker (i.e., the goals for all types of attacks for which the user wants to analyze the threat to the SHS). The DCM can be a DT algorithm, an LR algorithm, or a neural network algorithm (e.g., an artificial neural network algorithm). The ADM can be a DBSCAN algorithm or a k-means algorithm. For example, the DCM can be a DT algorithm and the ADM can be a DBSCAN algorithm.

BRIEF DESCRIPTION OF DRAWINGS

FIG. 14 shows a table of devices and parameters considered for monitoring health conditions.

FIG. 15 shows a table of modeling notations.

FIG. 16 shows a table of an attack scenario under an attack model.

FIG. 17 shows an example of decision tree constraints.

FIG. 18 shows an example of DBSCAN algorithm-driven constraints.

FIG. 19 shows a table of a comparison of the performance of machine learning algorithms for disease classification.

FIG. 20 shows a table of a comparison of the performance of machine learning algorithms for anomaly detection.

FIG. 21 shows a table of performance analysis of a pair of relationship models.

FIG. 22 shows a table of number of devices to comprise to achieve an attack goal.

FIG. 23 shows a table of complexity analysis of disease classification models (DCMs) based on the number of sensor measurements.

DETAILED DESCRIPTION

Figure 1:
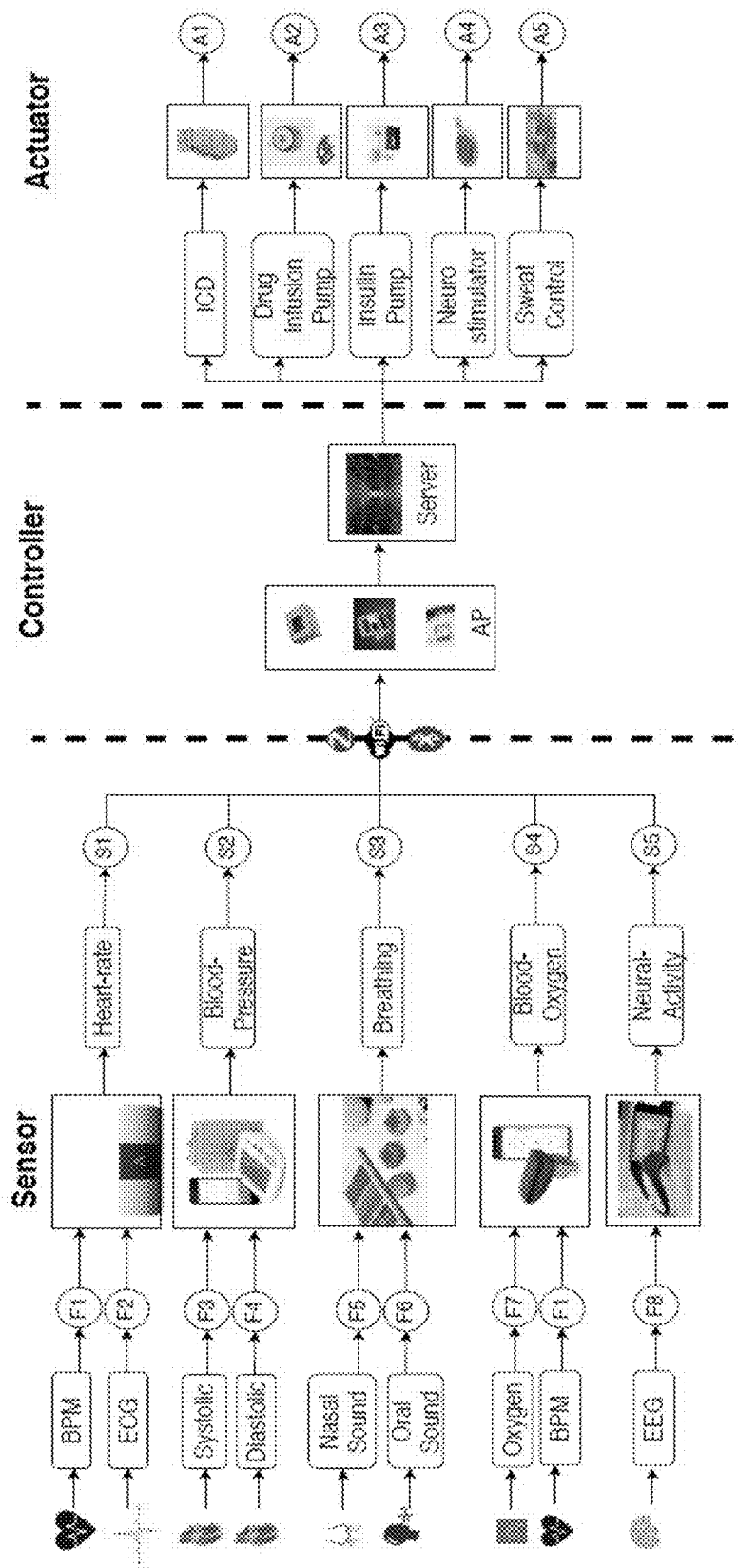
FIG. 1 shows a sensor behavioral model in smart healthcare systems (SHSs).

Embodiments of the subject invention provide novel and advantageous formal threat analysis systems (or analyzers) for smart healthcare systems (SHSs), as well as methods of using the same. The analysis system can formally analyze supervised and unsupervised machine learning (ML) models for SHS threat analysis. The system can analyze the underlying decision-making model of SHSs by investigating the possible attacks that can be deployed by minimal alteration of sensor values. Failures in safety-critical cyber-physical systems (CPSs), such as SHSs, can increase the possibility of life-threatening events. In order to increase reliability, SHSs often employ data validation or anomaly detection systems. Hence, the threat analysis system can consider a clustering-based anomaly detection model (ADM) in the SHS due to its real-time detection capability. The ADM can learn the pattern of sensor measurement relationships by analyzing data (e.g., a massive quantity of data). The system can assess potential attack vectors of an SHS that uses ML algorithms, such as decision tree (DT), logistic regression (LR), and/or artificial neural network (ANN) for classifying diseases, as well as K-means and/or density-based spatial clustering of applications with noise (DBSCAN) clustering algorithms for detecting anomalies. The system can focus on quantifying the associated threat that can be performed by minor alteration in one or more sensor measurements of an SHS. The system can advantageously acquire constraints from both supervised and unsupervised ML-based models (e.g., ML-based black box ML models) and anomaly detection systems.

Wireless body sensor networks (WBSNs) and implantable medical devices (IMDs)-based IoMT contribute significantly towards SHSs, allowing fast and efficient disease treatment. However, adversaries can launch various attacks on the communication network and the hardware/firmware to introduce false data or cause data unavailability to the automatic medication system endangering the patient's life. The threat analysis framework/system of embodiments of the subject invention (which can be referred to herein as "SHChecker") can integrate ML and formal analysis capabilities to identify potential attacks and corresponding effects on an IoMT-based SHS. The system can provide all potential attack vectors, each representing a set of sensor measurements to be altered, for an SHS given a specific set of attack attributes, allowing realization of the system's resiliency, and the insight to enhance the robustness of the model.

Related art threat analysis solutions focus on the network data assessment and adversarial ML-based models for vulnerability analysis in the network data and the vital sign measurements. However, no related art solutions provide a guarantee to identify all possible attacks based on the threat models. Systems of embodiments of the subject invention provide both speed and a guarantee to find all potential attack vectors, each representing a set of sensor measurements to be altered, for an SHS given a specific set of attack attributes. The system can focus on quantifying the associated threat that can be performed by minor alteration in one or more sensor measurements of an SHS.

Embodiments provide a fast and efficient threat analysis system (which can also be referred to herein as a framework or a threat analysis framework) that can obtain constraints from the underlying ML algorithm of SHSs for formal threat analysis. Sensitive sensor nodes in the SHS can be identified, which would otherwise pose a significant danger for the patients while their measurements are being compromised by adversaries. The threat analysis system can: provide insights about the vulnerability of the SHS; analyze robustness and/or resiliency of the SHS depending on the attacker's goal and accessibility; and/or propose an SHS reconfiguration scheme as an alternative formal architecture of the SHS, which would be susceptible to fewer threats.

IoMT-based SHSs are a game-changer for the medical field concerning consultation accuracy and cost reduction related to human labor. The enormous amount of medical data enables researchers to perform statistical analyses of diseases and medication patterns. With the introduction of IoMT in the healthcare field, more attention has been paid to developing ubiquitous data accessing solutions to acquire and process data from decentralized data sources. In the IoMT network, data are sent to a remote server to analyze and take control decisions due to the lack of processing capability of medical sensors and IMDs.

An IoMT applied SHS can incorporate a wireless body sensor network, an ML-based control system, and/or IMD-based actuators. FIG. 1 shows an SHS that can deliver medicine in real-time with a closed-loop decision control system without requiring any human involvement. In an SHS, patients are continuously monitored by the sensors attached to their bodies. These sensors deliver their observed measurements to the controller using, for example, a wireless communication protocol (e.g., WiFi, Bluetooth, Zigbee, etc.). The controller takes the measured values, makes decisions based on them, and sends the control commands to the IMDs to deliver the necessary treatment to the patient. For example, a patient's blood glucose monitoring system continuously advertises blood glucose value to the controller (see FIG. 14). The controller checks whether the vital signs of the patient are within normal ranges. If the controller determines that the patient needs emergency insulin delivery, it notifies the responsible insulin pump implanted inside the patient's body to inject the proper amount of medication.

ML algorithms can be used in critical applications where they drive decisions with enormous personal, organizational, or societal impact (e.g., healthcare). In a growing industry of healthcare sensors that continuously gather a plethora of health data, the prevalence of using ML to analyze these data is gaining momentum. An SHS model can use a disease classification model (DCM) and an ADM. The DCM can use a supervised ML algorithm that can label patient data accurately in real-time. ANN-based deep learning models and rules-based models like DT demonstrate moderate performance in disease classification. According to this classification, the controller makes decisions. The ADM uses an unsupervised ML technique to learn the complex relationship between various features and detect anomalous measurements. Usually, anomaly detection mechanisms take longer to execute because, most of the time, they do not provide any explicit model. The ADM verifies DCM-provided decisions.

Malware and man-in-the-middle (MITM) attacks are predominant in SHSs. One of the most recent malware attacks named "Medjack" (Medical Device Hijacking) exploits healthcare systems by placing malware within the IoMT networks (see also Storm, Medjack: Hackers hijacking medical devices to create backdoors in hospital networks, computerworld.com/article/2932371/medjackhackers-hi-jacking-medical-devices-to-create-backdoors-in-hospital-networks.html, 2015; which is hereby incorporated by reference herein in its entirety). Medjack is a stealthy cyber-attack that utilizes the concept of polymorphic malware by constantly escalating its capability, making it very difficult to get revealed. By creating a backdoor behind the firewall, Medjack gains access to the network without being detected.

MITM is a cyber-attack where an adversary illegally gets into the communication between two authorized parties and eavesdrops on the transmitted data or corrupts it. Bluetooth-enabled medical devices exhibit potential vulnerabilities in sensor networks. An MITM attack can be launched, for example, in a Bluetooth-enabled pulse oximeter, which means that medical sensors can be compromised (see also Pournaghshband et al., Securing legacy mobile medical devices. In International Conference on Wireless Mobile Communication and Healthcare, pages 163-172, Springer, 2012; which is hereby incorporated by reference herein in its entirety). The MITM attacks on wireless links can be performed in various ways, for example by jamming Bluetooth pairing with devices or access points (APs).

Threat modeling is the process of potential threat recognition and security measures to protect a valuable system. Embodiments of the subject invention provide a threat analysis model considering data corruption, MITM, and malware injection attacks that can compromise SHS sensor values without getting detected by the system to prevent or inhibit providing intended service from a system or cause the wrong service to be delivered. In the threat analysis model, a powerful attacker can be considered who can eavesdrop and alter sensitive safety-critical data in such a way that provokes the control system to make a wrong decision.

An attacker's capabilities specify the appropriate ways (e.g., knowledge, time, expertise, and tools) and opportunities (e.g., enough time to perform the attack) to exploit the vulnerabilities that can materialize possible threat. Embodiments of the subject invention provide a threat model that identifies potential attack vectors, which could otherwise significantly affect the system's consistency and increase the probability of inaccurate medication delivery.

Figure 2:
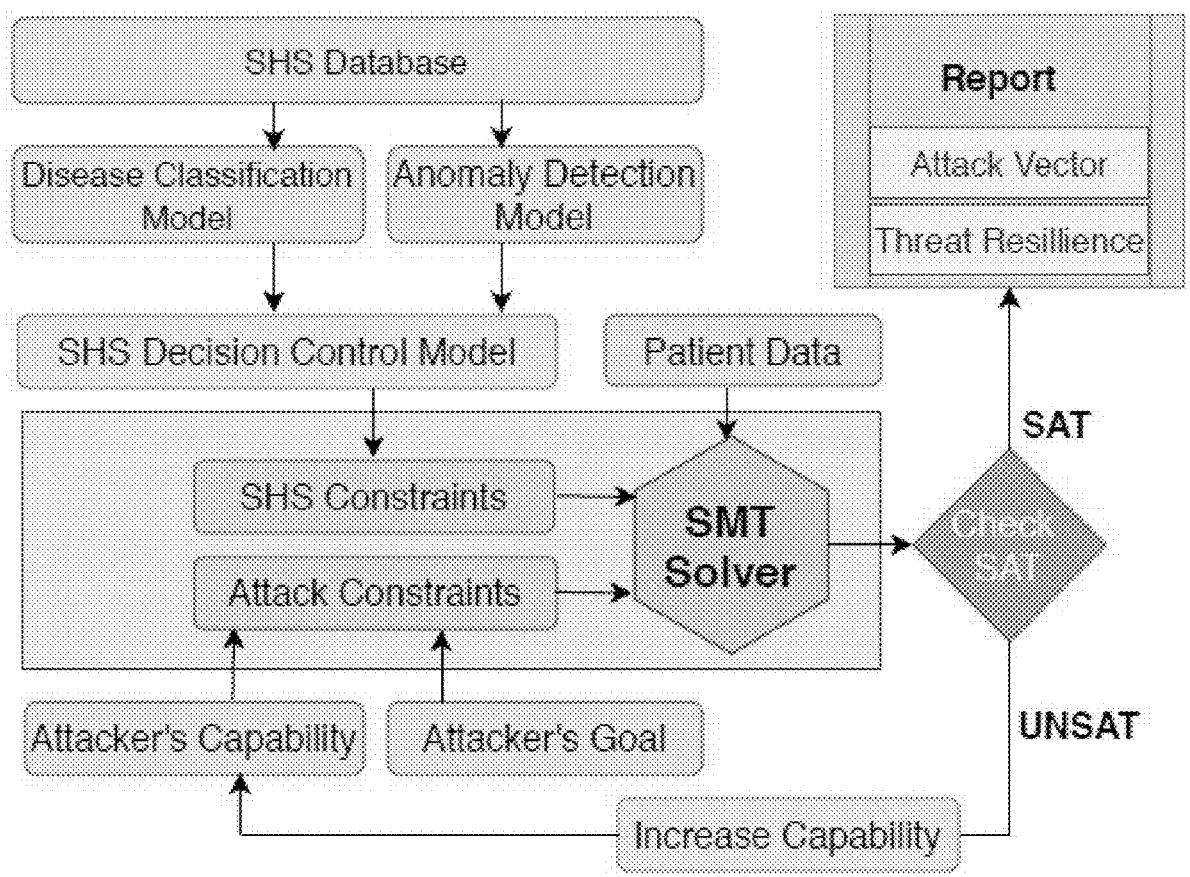
FIG. 2 shows a schematic view of the architecture of a system for threat analysis, according to an embodiment of the subject invention.

FIG. 2 shows a schematic view of the architecture of a system for SHS threat analysis, according to an embodiment of the subject invention. Referring to FIG. 2, the smart healthcare dataset can first be provided/fed to train two ML models. The DCM can be trained to label the patients, and the ADM can verify the consistency of the sensor data for that specific level. The outputs from these two models can be used in the SHS decision control model. The decision control model can process the inputs from the ML models into decision boundaries and generate necessary constraints accordingly. Then, a satisfiability modulo theory (SMT) solver can take all the constraints associated with the SHS model and the attacker's capability and goal, along with the sensor/measurement data of a patient, as input, and encode the analysis of the attack feasibility as a constraint satisfaction problem (CSP).

The SMT solver can utilize various background theories to solve the CSP. When it returns a "satisfactory" (SAT) result, it implies that the given set of constraints is satisfied for the patient data into consideration. A SAT result reports an attack vector that includes a set of values to be injected to a set of sensor measurements for misclassifying the given patient data based on the attacker's goal. The framework/system can choose the attacker's capability in a systematic way so that a SAT result at the minimum capability can be received. In this case, the attack vector also implies that the attacker cannot succeed in his goal if his capability is lower than the system/framework-reported capability. Hence, the SHS can be defined as threat resilient until that attack's capability in terms of cybersecurity.

An "unsatisfactory" (UNSAT) result by the SMT solver signifies that the attack cannot possibly attain the attacker's goal based on the given capabilities. In such a case, the system/framework can increase the attacker's capability by providing him/her with access to more resources, reexamine the attack feasibility, and repeat the process until successful in finding an attack vector or until the attacker's capability can no longer be increased.

The SHS threat analysis framework can include two major functional components: ML model(s); and a formal analysis model.

Machine Learning Model

The system/framework can perform a threat analysis of two different types of ML-based models, DCM and ADM. The DCM can consider three widely-used algorithms, namely decision tree (DT), logistic regression (LR), and neural network (NN). DBSCAN and K-means clustering-based models can be adopted for the ADM.

DT is a classification model that is comprehensive, fast, easy to use, and has a versatile nature. DT produces a tree data structure like decision rules to devise a category based on the dataset features. Determining the feature selection order and finding the best splitting points are the main challenges to generate the inference rules. These challenges are referred to as attribute selection in machine learning. Various metrics are used for attribute selection, such as information gain, Gini index, and others. In some embodiments, DT can be implemented using the Classification and Regression Trees (CART)-based algorithm and can consider the Gini index metric for attribute selection.

LR models are efficient baseline models for solving classification problems, which work better for drawing accurate decision boundaries between various classes when the relationship between features and labels are straightforward. As LR is mainly designed for solving binary classification problems, selecting a multiclass classification approach presents significant challenges. LR uses various solvers to optimize cost function for finding the best decision boundary. In frameworks of embodiments of the subject invention, the one versus rest scheme can be used for performing multiclass classification, and the limited-memory Broyden-Fletcher-Goldfarb-Shanno solver can be used for optimizing the classification's cost function problem (see also Retno et al., Limited memory broyden-fletcher-goldfarb-shanno (1-bfgs) method for the parameter estimation on geographically weighted ordinal logistic regression model (gwolr), In AIP Conference Proceedings, volume 1868, page 040009, AIP Publishing LLC, 2017; which is hereby incorporated by reference herein in its entirety).

Artificial Neural network algorithms can replicate the human brain and perform multiple tasks parallel to retaining system performance. Most importantly, unlike LR, NN can discover intricate patterns from data. NN models work remarkably well for multiclass classification problems, although training such a model requires a lot of tuning such as learning rate, batch size, number of hidden layer, and others. The SHChecker framework can use a feed-forward NN that optimizes its cost function using an adam optimizer.

The DBSCAN algorithm can be considered for the ADM, as it shows promising performance for finding anomalies. DBSCAN splits the dataset into several clusters using two hyperparameters—epsilon and minpoints (the minimum number of points to create a cluster). Any point that does not fit into any cluster is denoted as a noisy point. Frameworks of embodiments of the subject invention can group the good data points based on DT labels and find the optimal values for the parameters to cluster all the good data points. Though, DBSCAN does not give any explicit decision boundary for those clusters.

K-means algorithm is another unsupervised clustering algorithm that creates a given number of the cluster over the data samples applying the data's mean. Unlike the DBSCAN algorithm, determining the optimal number of clusters, k, is a big challenge in the K-means algorithm. The K-means algorithm does not come up with an explicit decision boundary as well. In embodiments of the subject invention, the Euclidean distance metric can be used for both DBSCAN and k-means.

All of these algorithms leverage the relationship between the features. The decision rules from the DCM can be used to produce constraints associated with the SHS. However, in order to generate data validity of cluster-derived constraints from the anomaly detection algorithm, the decision boundary needs to be defined formally. A concave hull algorithm can be used to get a tight bound for the clusters (see also Moreira et al., Concave hull: A k-nearest neighbours approach for the computation of the region occupied by a set of points, 2007; which is hereby incorporated by reference herein in its entirety). The concave hull algorithm uses a k-nearest neighbor-based approach to fit the data points in a best-described polygon concave polygon that can be smoothed by a hyperparameter, k (see also Guo et al., Knn model-based approach in classification, In OTM Confederated International Conferences, On the Move to Meaningful Internet Systems, pages 986-996, Springer, 2003; which is hereby incorporated by reference herein in its entirety).

Formal Analysis Model

The frameworks of embodiments of the subject invention can perform a formal analysis by modeling the problem as a CSP that considers two kinds of constraints associated with modeling: (i) the SHS; and (ii) attacks. The table in FIG. 15 shows the notation used herein for formal modeling.

For formal modeling of the SHS, let us assume that P is the set of sensor measurements of a patient with a patient status/label, j. In order to verify the authenticity of the sensor measurements and the label, the SHS model can be used. If the data satisfies both disease classification and ADM-driven constraints, it can be considered as validated for the patient's status.

Next, the derivation of classifier-driven constraints will be discussed. With respect to DT constraints, a decision tree model returns an inference hierarchical rules-based model, from which formal model constraints acquisition to represent the model is quite straight-forward. A boolean function inference(P, j) returns True if sensor values are consistent with label j for DT inference rules.

Figure 3:
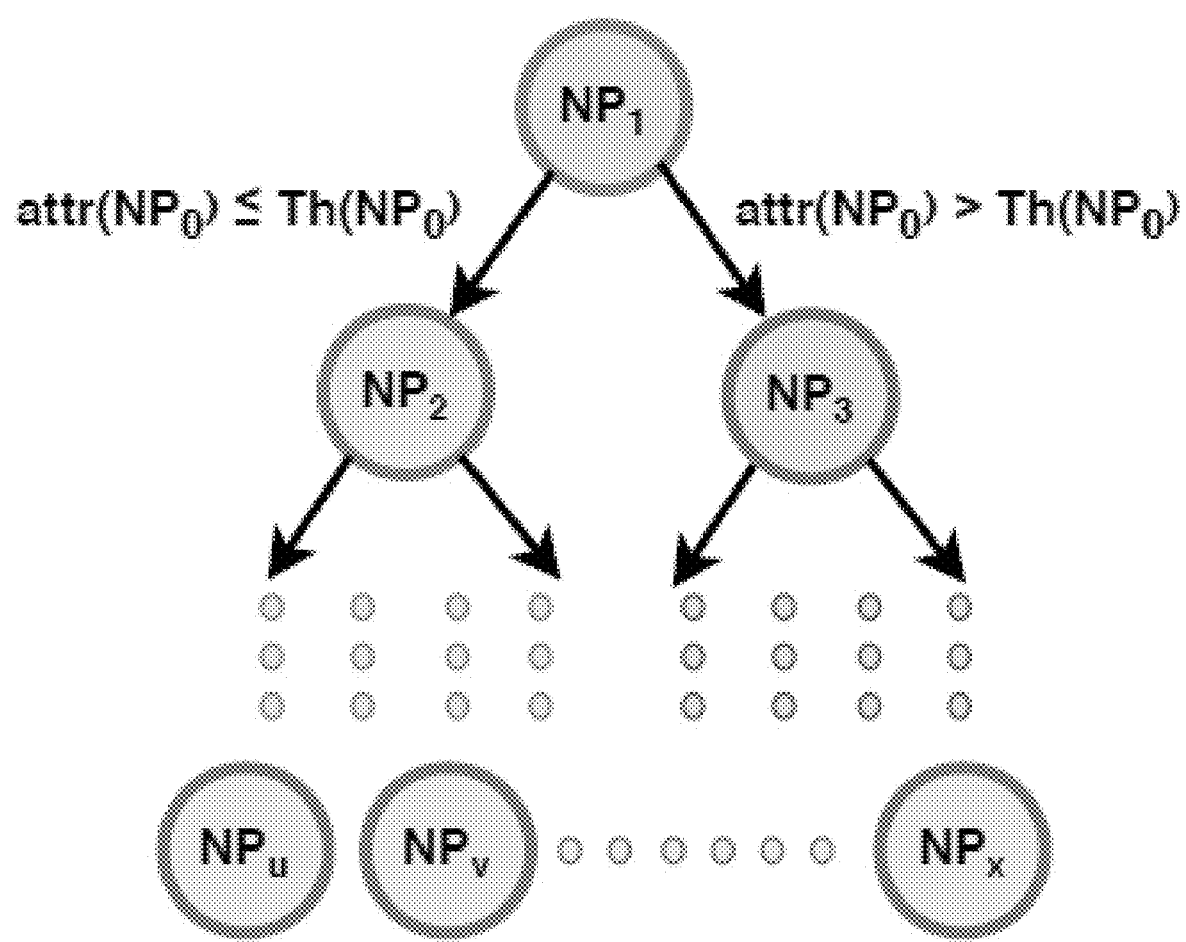
FIG. 3 shows a hierarchical representation of a decision tree.

DT contains several nodes starting from the root node. Each node of the tree includes an attribute that denotes a sensor measurement which is used to split the tree at that point with a threshold value. A patient's sensor measurement of that particular attribute having greater than the threshold follows the right path at that particular node, and otherwise it follows the left path. This attribute and the threshold value generate a rule as shown in Equation 1. FIG. 3 demonstrates a decision tree model to help understand the DT constraints.

$$\text{rule}(\mathcal{P}_a, d, e) = \begin{cases} \mathcal{P}_a \leq Th(d) & \text{if } e \text{ is a left node of } d \\ \mathcal{P}_a > Th(d) & \text{if } e \text{ is a right node of } d \end{cases} \quad (1)$$

Here, e is an immediate child of d and a=attr(d).

The whole tree is divided into multiple paths, from the root to the leaf. Each path has a label and set of rules along its way. Equation 2 demonstrates the process of determining rules from a set of rules along a path.

$$\text{rules}(\mathcal{P}, f) = \bigwedge_{i=1}^{|Np^f|-1} \text{rule}\left(\mathcal{P}_{attr(Np_i^f)}, Np_i^f, Np_{i+1}^f\right) \quad (2)$$

The decision tree assigns a label j as patient status if and only if sensor measurements associated with that patient satisfy all inference rules along a path having label j. Here, j is the label of the last node of the path.

$$\text{inference}(P, j) \Leftrightarrow \exists_{f \in Pth} \text{label}(f) = j \text{'rules}(P, f) \quad (3)$$

With respect to LR constraints, a logistic regression model assigns some probability values to each patient status for a patient. The label that gets the highest probability after applying the softmax function is selected as that patient status. The model parameters, in this case, have been obtained by minimizing a cost function for optimal decision boundary using maximum log-likelihood. The inference constraints for LR are shown in Equation 4.

$$\text{inference}(\mathcal{P}, j) \Longleftrightarrow \underset{g}{\operatorname{argmax}} \frac{\exp\left(\left(\sum_{i=1}^{n_s} \mathcal{P}_g \theta_{gi}\right) + \epsilon_g\right)}{\sum_{h=1}^{n_l} \exp\left(\left(\sum_{i=1}^{n_s} \mathcal{P}_h \theta_{hi}\right) + \epsilon_h\right)} = j \quad (4)$$

With respect to NN constraints a neural network model comprises a number of layers that can include an input layer, one or more hidden layers, and one output layer. The input of each node at any layer except the input layer is calculated from the previous layer's output, weights, and bias. Suppose, N=|NL|, number of layers in the model.

$$\forall_{m \in (1,N]} \text{input}(NL_{mn}) = \sum_{o=1}^{|NL_{m-1}|} \left(\text{output}(NL_{(m-1)o}) \times W_{on}^{m-1}\right) + b_{mn} \quad (5)$$

Figure 4:
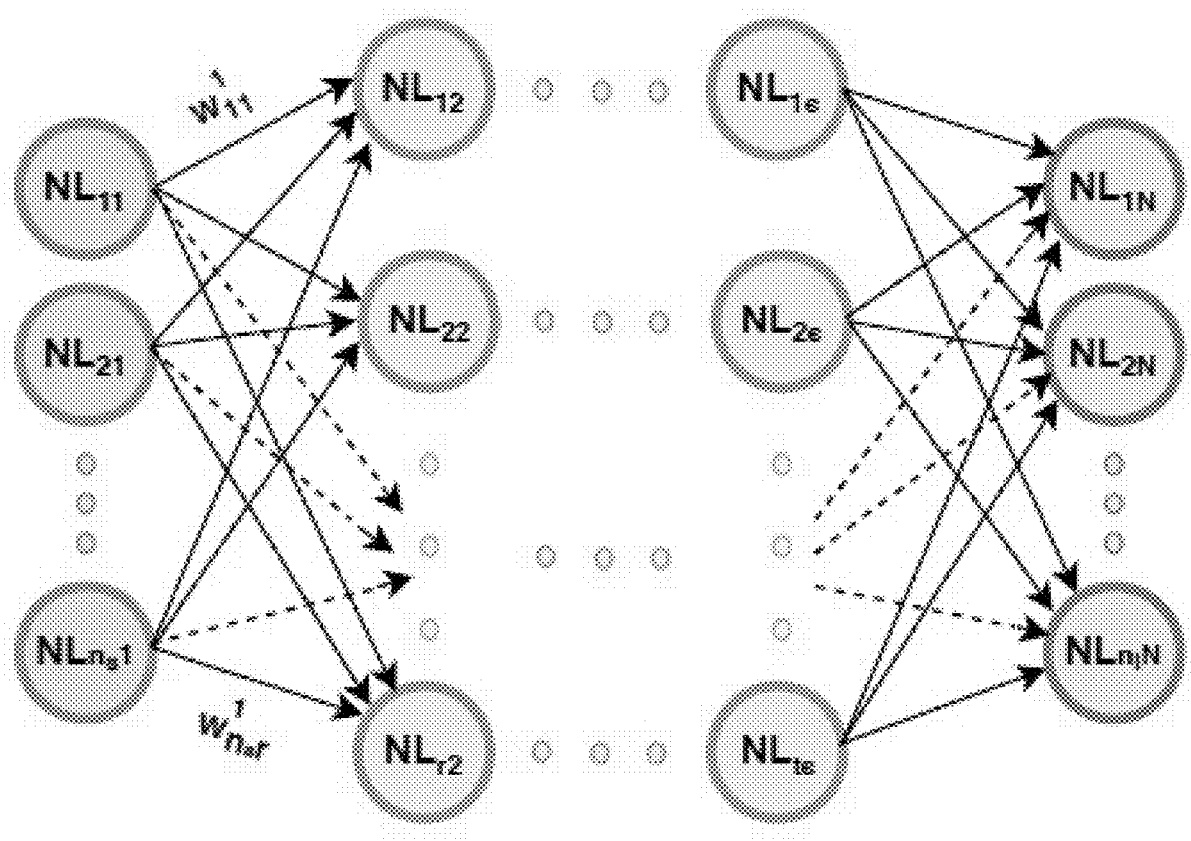
FIG. 4 shows a network diagram of a neural network model.

The input and output of layer 1 are the sensor measurement values as shown in Equation 6. FIG. 4 demonstrates a neural network model of N layers where the last hidden layer is denoted by €, i.e., €=N−1.

$$\text{input}(NL_1) = \text{output}(NL_1) = P \quad (6)$$

In order to calculate each node's output, input values of a particular node are passed through a complex activation function such as rel u or tan h.

$$\forall_{m \in (1,N]} \text{output}(N L_{mn}) = \text{activation}(\text{input}(N L_{mn})) \quad (7)$$

Label j is assigned to the patient in consideration if and only if the softmax function outcome of the $j^{th}$ output node has a higher value than the other output nodes.

$$\text{inference}(\mathcal{P}, j) \Longleftrightarrow \underset{g}{\operatorname{argmax}} \frac{\exp(\text{input}(NL_{ng}))}{\sum_{q=1}^{n_l} \exp(\text{input}(NL_{nq}))} = j \quad (8)$$

Next, the derivation of algorithm-based constraints will be discussed. In order to validate the consistency of a set of measurements, DBSCAN algorithm-driven constraints can be used. Consistency between the combination of all pairs of sensor measurements can be considered, instead of all sensor measurements together, to face the challenge of obtaining constraints in high dimensional space. Because most of the clusters do not satisfy the requirement of constraint acquisition in high dimensional space due to lack of sufficient cluster data points, these constraints can be found according to the logical functions of checking if the measurements are within that specific label's clusters. This concept can be demonstrated with an example.

Figure 5:
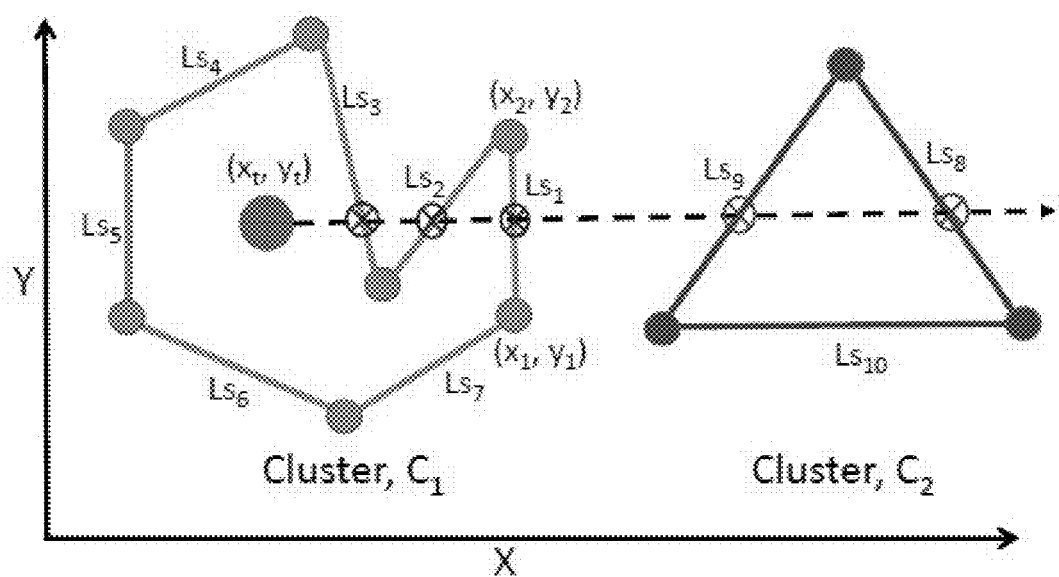
FIG. 5 shows a plot visualizing the logic behind checking if a point is inside a polygon cluster in a density-based spatial clustering of applications with noise (DBSCAN) algorithm.

FIG. 5 shows two clusters ($C_1$ and $C_2$) in a two-dimensional (2D) data plane where $C_1$ has seven line segments ($Ls_1, Ls_2, \ldots, Ls_7$) and $C_2$ has three line segments ($Ls_8, Ls_9,$ and $Ls_{10}$). The end points of any line segment ($Ls_i$) can be denoted as ($x^i_a, y^i_a$) and ($x^i_b, y^i_b$), where $y^i_b \geq y^i_a$. In order to validate the consistency of a data point (x, y), the following logical functions can be used: inRangeOfLineSegment (x, y, $Ls_i$); leftOfLineSegment(x, y, $Ls_i$); intersect(x, y, $Ls_i$); and/or withinCluster(x, y, $C_k$).

The inRangeOfLineSegment (x, y, $Ls_i$) function checks whether the point is within the vertical range of the line segment, $Ls_i$.

$$\text{inRangeOfLineSegment}(x,y,LS_i) \Leftrightarrow y_a^i < y \leq y_b^i \quad (9)$$

Thus, referring to FIG. 5, it can be said that, inRangeOfLineSegment($x_t, y_t$, $Ls_1$) returns True for a point ($x_t, y_y$) as $y_t$ is within the range of $y^1_1$ and $y^1_2$. However, for line segment $Ls_4$, inRangeOfLineSegment($x_t, y_t$, Ls4) returns False as $y_t$ is not in the vertical range.

The leftOfLineSegment(x, y, $Ls_i$) function checks if the point (x, y) is on the left side of the line segment, $Ls_i$.

$$\text{leftOfLineSegment}(x,y,Ls_i) \Leftrightarrow (x(y_a^i - y_b^i) - y(x_a^i - x_b^i) - (x_a^i y_b^i - x_b^i y_a^i)) < 0 \quad (10)$$

For cluster $C_1$ in FIG. 5, leftOfLineSegment($x_t, y_t$, $Ls_1$) returns True while leftOfLineSegment($x_t, y_t$, $Ls_5$) returns False.

With respect to intersect(x, y, $Ls_i$), an imaginary line is drawn from the point (x, y) to the right side, which is also parallel to the x-axis. The function intersect determines if the imaginary line intersects the line segment, $Ls_i$. The imaginary line intersects the line segment only when the point (x, y) is within the range of the line segment and also located on the left side of it. The function is formalized as follows:

$$\text{intersect}(x,y,Ls_i) \Leftrightarrow \text{inRangeOfLineSegment}(x,y,Ls_i) \hat{} \text{leftOfLineSeegment}(x,y,Ls_i)$$

From FIG. 5, it can be seen that intersect($x_t, y_t$, $Ls_i$) returns True only for line segments 1, 2, 3, 8, and 9.

The withinCluster(x, y, $C_k$) function returns True if the data point (x, y) is within the cluster, $C_k$. For all the (boundary) line segments ($Ls_i$) of $Ls_i$, the function calculates intersect(x, y, $Ls_i$) and performs the XOR operation on them. If there are an odd number of intersections with the line segments, withinCluster returns True as the XOR operation on one or more False values and an odd number of True values results True. Thus, the function can be defined as:

$$\text{withinCluster}(x, y, C_k) \Longleftrightarrow \bigoplus_{1 \leq i \leq numOfLs_{C_k}} (\text{intersect}(x, y, Ls_i) \wedge In(C_k, Ls_i)) \quad (12)$$

Here, In($C_k$, $Ls_i$) checks whether the line segment, $Ls_i$ is from the cluster $C_k$ or not. In FIG. 5, ($x_t, y_t$) is inside cluster $C_1$, as the imaginary line parallel to axis x from it intersects an odd number (three) of line segments of the cluster. On the other hand, the imaginary line intersects two line segments of cluster $C_2$, and thus, the data point is outside of the cluster $C_2$.

With respect to formal modeling, let it be assumed that a total of $n_s$ different sensor measurements are captured from the body of a person, and he/she possesses a health state from the $n_l$ labels. Without the loss of generality, let it be assumed that each measurement is recorded/reported by one sensor. Let S be the set of all the sensors, P be the set of measurements of those sensors, and L be the set of all possible labels for a person. Let the current label of the person be j, where j∈L. In order to keep the clustering simple (2D) along with the associated constraints, the relationship of two sensors at a time can be considered. Thus, for the label j∈L and sensor pair (a, b) where (a, b)∈S, one or more clusters, $C_k^{a,b,j}$ can be obtained, representing the relationship between the two measurements for that specific label. These clusters include a few line segments, which are represented as $Ls_l^{a,b,j}$. In order to check the consistency of the data measurements with the constraints from DBSCAN, take pair of two sensor measurements $P_{a,b}=(P_a, P_b)\in P$. The consistency of measurement set P can be verified by checking if each pair of measurements is within any of the corresponding clusters, $C_k^{a,b,j}$. The measurement set is consistent if the following condition holds:

consistent(P,j)⇔∀$_{(a,b)\in s \wedge (a!=b)}$∃$_{k\in C}$
    withinCluster($P_{a,b},C_k^{a,b,j}$)

where
withinCluster($P_{a,b},C_k^{a,b,j}$)⇔

$$\bigoplus_l \left( \text{intersect}(\mathcal{P}_a, \mathcal{P}_b, Ls_l^{a,b,j}) \wedge In(C_k^{a,b,j}, Ls_l^{a,b,j}) \right) \quad (14)$$

and intersect($P_a,P_b,Ls_l^{a,b,j}$)⇔inRangeOfLineSegment($P_a$,
    $P_b$),$Ls_l^{a,b,j}$)^leftOfLineSegment($P_a,P_b$),$Ls_l^{a,b,j}$)   (15)

K-means algorithm-based constraints acquisition requires a similar approach as constraint acquisition of the DBSCAN algorithm. Due to the algorithmic variation, the number of clusters, number of noise points, and clusters' points are different.

With respect to formal modeling of attacks, formal models allow for exploration of the search space of all possible behaviors of the system and figuring out of potential vulnerabilities. The attack model can take the attacker's goal, attacker's capability, and the underlying model of the system as input and can formally model them and find out possible threats using the satisfiability modulo theory (SMT). The frameworks of embodiments of the subject invention aim to achieve the attacker's goal compromising a minimum number of sensors within the attacker's capability as well. The attacker's capability is dependent on the range of values that can be changed without alarming the system.

With respect to the attacker's goal, it can be considered that an adversary attempts to compromise the system so that the control system misclassifies the patient and supplies incorrect medication. The frameworks of embodiments of the subject invention can come up with all possible attack vectors. An attack vector reveals the complete path of launching an attack. An attacker can change a patient's label from j to ĵ if the following constraint is satisfied.

alter(j,ĵ)→∀$_{s\in S}(P_s→P_s+\Delta P_s)$^inference(P,j)^
    consistent(P,j)^inference(P,ĵ)^consisent(P,ĵ)   (16)

Equation 16 requires both the current and altered labels to be satisfied by the classification model and ADM constraints. Here, $P_s$, $\Delta P_s$, and $P(bar)_s$ represent the actual, amount of change, and altered measurement value, respectively, of sensor s.

With respect to attacker's accessibility, an attacker can change a sensor measurement if he/she has access to that particular sensor.

$$\forall_{s\in S} a_s \rightarrow (\Delta P_s \neq 0) \quad (17)$$

Here, $a_s$ is converted to integer, where false is replaced by 0 and true is transformed into 1.

With respect to attacker's capability, an attacker may not be able to launch a successful attack by modifying one sensor value only. The formal model can specify how much of the resources can be accessed and tempered by the attacker.

$$\sum_{s\in S} a_s \leq \text{Maxsensors} \quad (18)$$

$$\forall_{s\in S} \text{ abs}\left(\frac{\Delta \mathcal{P}_s}{\mathcal{P}_s}\right) < \text{Threshold} \quad (19)$$

Here, Maxsensors can limit the maximum number of sensors accessible by the attacker, and Threshold denotes the allowed range of measurement alteration for achieving the attack goal without getting revealed. Even if compromised sensor measurements of a successful attack come from an existing cluster following all ADM constraints, drastic alteration (compared to recent values) may create suspicion to the controller. Thresholds are considered for ensuring a stealthy attack.

With respect to attack matrix, the framework of embodiments of the subject invention can generate an attack matrix that associates the complete attack vector with all possible attack goals from a specific label that can be launched with the minimal capability of the attacker. Attack Matrix can also express whether it is feasible to attain a certain goal.

Embodiments of the subject invention provide a framework/system that performs formal threat analysis of an SHS (e.g., a black-box SHS) incorporating two different purpose ML-based models. The framework/system provides an ML and formal modeling-based framework to model and study the security of SHSs. The tool can analyze the potential threats that satisfy the attacker's goal. ML can be used to understand the relationships between the sensor measurements, health states, and their consistency. This knowledge can be exploited to perform formal analysis to synthesize potential attack vectors for a given attack model, where the attacker can change the health state (the actual one) to an incorrect state (the targeted state). The experimental results on two datasets show that diverse attacks are possible by compromising different numbers and types of sensor values, even compromising only one sensor measurement (see Examples 1-9).

Embodiments of the subject invention are useful for cyber-security, automated patient monitoring and treatment (e.g., amputated patient treatment, anesthesia patient monitoring, automatic pill delivery system), and medical devices. Embodiments of the subject invention can formally analyze supervised and unsupervised ML models for black-box SHS threat analysis. Embodiments of the subject invention can use an ML-based DCM to deliver real-time treatment, and can analyze the underlying decision-making model of SHS by investigating the possible attacks that can be deployed by minimal alteration of sensor values. SHSs often employ data validation or anomaly detection systems, and embodiments of the subject invention can therefore use a clustering-based anomaly detection model (ADM) in the SHS due to its real-time detection capability. The ADM can learn the pattern of sensor measurement relationships by analyzing a massive quantity of data. The framework can assess potential attack vectors of an SHS that uses ML algorithms, such as DT, LR, or NN (e.g., artificial NN (ANN)) for classifying diseases and k-means or DBSCAN clustering algorithms for detecting anomalies. The framework can quantify the associated threat, which can be performed by minor alteration in one or more sensor measurements of an SHS.

Embodiments of the subject invention provide modeling of a real-time SHS by deploying a DCM and a corresponding ADM. The attack model for an SHS can be formally represented (or modeled) using a set of flexible attack attributes that specifies an attacker's capabilities and the attack target. A threat analysis framework (SHChecker) can identify potential attack vectors for an ML model-based SHS (see also, github.com/anonymous1307019/SHChecker; which is hereby incorporated by reference herein in its entirety).

Embodiments of the subject invention provide a focused technical solution to the focused technical problem of securing an SHS from potential attackers. This has many uses, including increasing the safety for patients using the SHS, as it decreases the chances of an attacker altering the diagnosis and/or treatment for the patient(s). Embodiments of the subject invention also improve the computer system on which the algorithms are running because the threat analysis framework can identify potential attacks with ML models in an efficient manner, thereby conserving computing resources. The threat analysis framework of embodiments of the subject invention also improves the SHS on which it is utilized by providing all potential attack vectors (each representing a set of sensor measurement to be altered), thereby realizing and improving the system's resiliency and/or safety.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., sub-ranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Materials and Methods

In the threat analysis model, it can be presumed that the attacker has complete knowledge of SHS architecture and inter-sensor dependencies and also has access to the points for compromising data. The attacker can alter sensor measurements to deliver incorrect medication by compromising the underlying DCM. It can be assumed that controllers and actuators are secured/protected against being comprised directly. Moreover, as the SHS IoMT network sensors cannot consume a significant amount of energy, they are unable to send or receive encrypted data due to the limitation of computation power. An attacker can exploit this vulnerability and launch an attack to compromise the consistency of the system. Two case studies can be considered for evaluating the framework. In both of the case studies, an SHS with DT-based DCM and DBSCAN-based ADM can be considered, as these two ML algorithms performed better than the other considered algorithms based on our experimentation.

In a first case study, in order to verify SHChecker, a realistic healthcare dataset was developed with eight sensor measurements with 17,000 samples after preprocessing. In the processed dataset, a total of 6 labels of various patient statuses were used. FIG. 16 shows the measurements of four sensors of a particular patient. According to the attack vectors identified by the SHChecker, in order to misclassify a high blood cholesterol labeled patient into a high blood pressure one, compromising only one sensor cannot achieve the attack goal. However, the attacker can be successful by compromising two sensors (e.g., systolic blood pressure and blood oxygen) if only the DT model is considered for threat modeling. However, the combined model of embodiments does not comply with this. The combined DT and DBSCAN cluster-based algorithm shows that at least four sensors need to be compromised to achieve the goal, which confirms the ADM's necessity in the SHS. Using the combined model, an attack vector can be found by changing the heart rate sensor value by 2.12%, systolic blood pressure by 7.17%, diastolic blood pressure value by 2.53%, and blood oxygen measurement value by 5.68%. FIGS. 17 and 18 show some example DT constraints and DBSCAN constraints, respectively, obtained from the formal threat model.

In a second case study, in order to verify SHChecker, the framework has been implemented in a real-world dataset collected by The University of Queensland (see also Liu et al., University of queensland vital signs dataset: development of an accessible repository of anesthesia patient monitoring data for research, Anesthesia & Analgesia, 114(3): 584-589, 2012; which is hereby incorporated by reference herein in its entirety). The dataset contains 49 sensor measurements of 32 anesthesia patients with surgical cases at the Royal Adelaide Hospital, monitored using Philips intellivue monitors and a Datex-Ohmeda anesthesia machine. After preprocessing, the dataset containing 209,115 samples with 26 sensor measurements was used to find attack vectors using the SHChecker framework. Based on the vital signs of the patients, the monitoring systems issue single or multiple alarms. In the processed dataset, a total of 58 labels having 28 different alarms was obtained. Out of these labels, 24 dealt with a single alarm, 19 handled a couple of alarms, 12 of them provided triple alarms, and the rest involved quadruple alarms. Using the threat model, the feasibility of compromising the system was checked by providing the wrong alarm. The experimentation showed that by altering 9.2%, 8.1%, 8.4%, 2.3%, 5.9%, 9.9%, 2.1%, 3.9% values in artery diastolic pressure (ART Dia), artery mean pressure (ART Mean), effective end-tidal decreased hemoglobin oxygen saturation (ETDES) label, inspired de-creased hemoglobin oxygen saturation (INDES) label, end-Tidal isoelectric (ETISO) point, inspired isoelectric (INISO) point, effective end-tidal concentration of sevoflurane (ETSEV), and inspired concentration of sevoflurane (INSEV) sensors, respectively, an adversary can make the system trigger APNEA, low blood pressure (NBPsLOW), low end-tidal carbon-dioxide (etCO2LOW), high inspired concentration of sevoflurane (in-SEVHIGH) alarm instead of APNEA, high minute volume (MVexpHIGH) by compromising both DT and DBSCAN-based control algorithms.

Figure 6A:
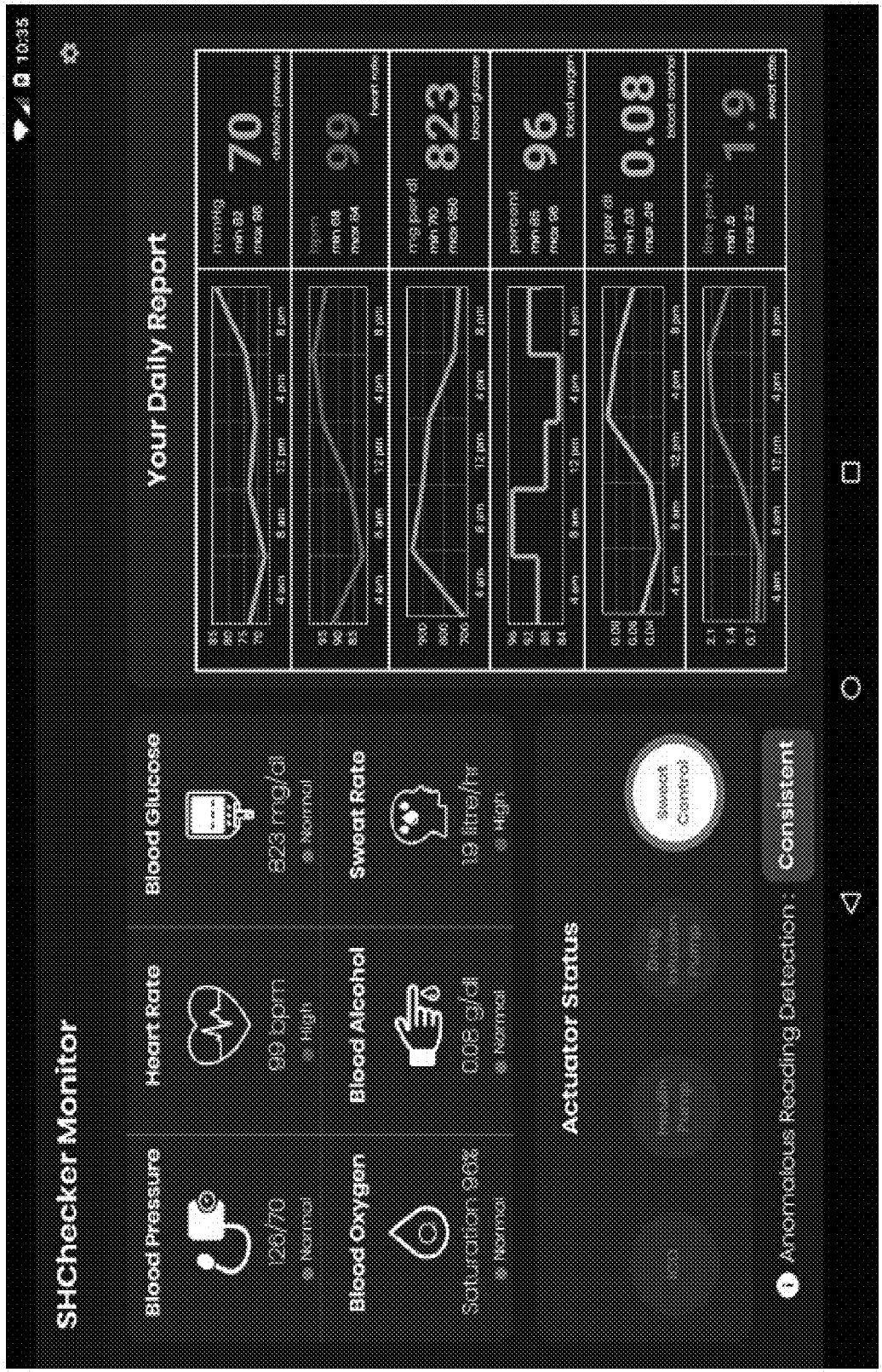
FIG. 6A shows an image of a patient monitor, according to an embodiment of the subject invention.
Figure 6B:
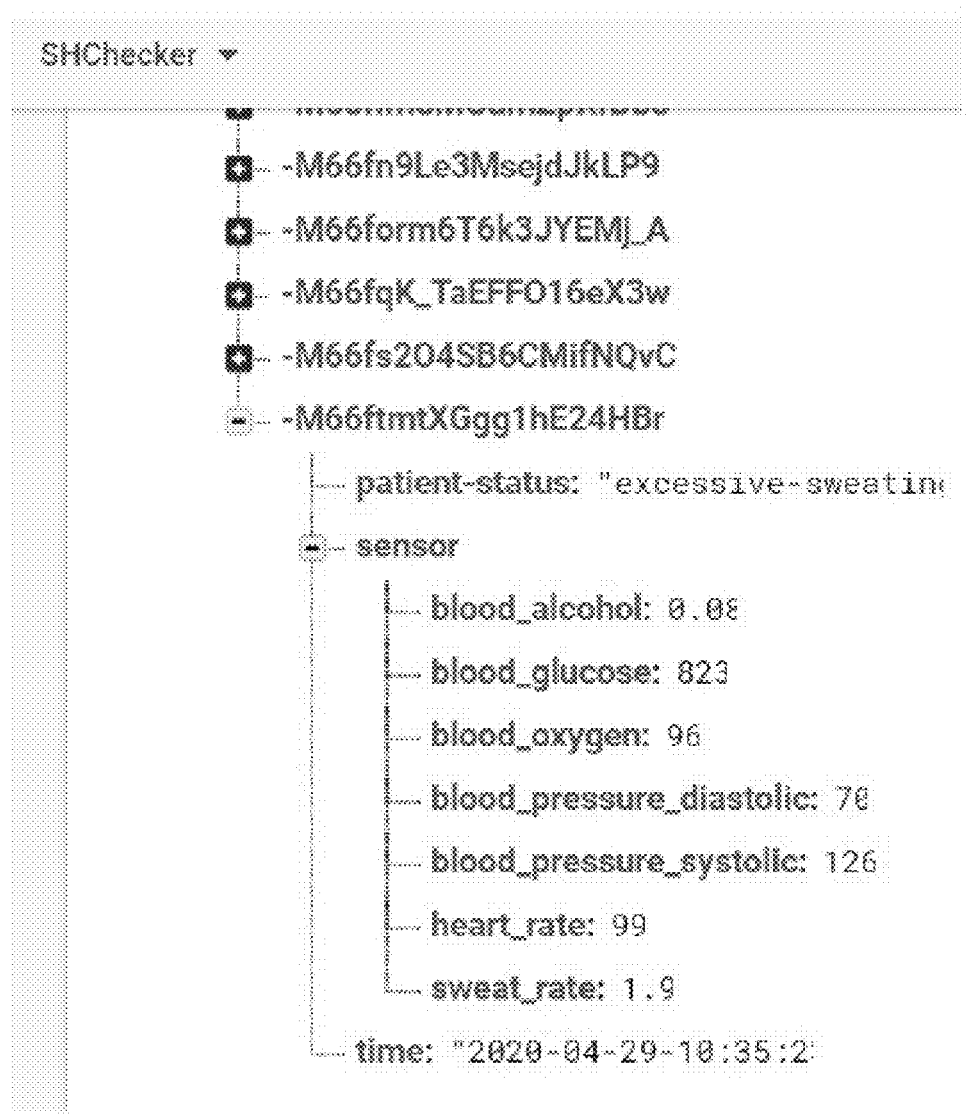
FIG. 6B shows an image of a snapshot of a database, according to an embodiment of the subject invention.
Figure 7:
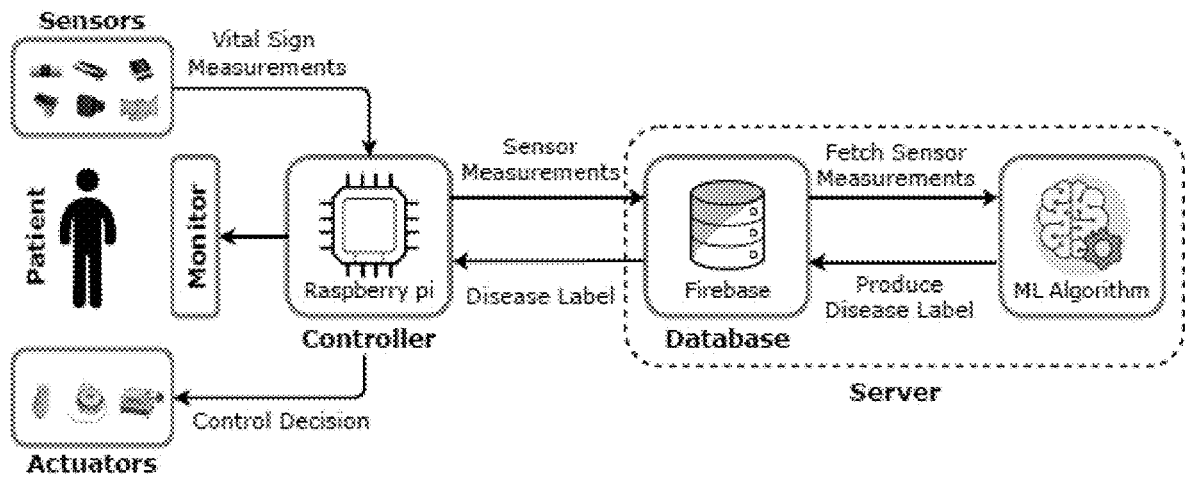
FIG. 7 shows a schematic view of testbed implementation of a system according to an embodiment of the subject invention.

In order to verify the SHChecker framework, an SHS testbed was implemented considering a patient being connected to an IoMT network and being continuously monitored with six different body sensors while getting real-time treatment with four actuators. FIG. 7 shows the testbed setup where the sensors and the actuators are connected with a raspberry pi-based controller. The controller receives the sensor values by maintaining a specific time interval as the sampling rate of the sensors is different and acquires the disease label from the machine learning algorithms running inside the server. The controller and the server exchange data using a real-time (firebase) NoSQL database as it is difficult to handle data generated by the IoT system with traditional databases. An android application was developed that works as a patient monitor showing sensor measurements and the respective statuses of the IMD devices. In the monitor, the sensor values and the actuators triggered by the controller are shown. FIG. 6A displays a snapshot of the android application for patient monitoring, and FIG. 6B exhibits NoSQL data structure from the firebase database for storing patients vital sign data.

The SHChecker framework was evaluated in view of the following considerations: impacts of using a disease classification and anomaly detection-based combined model instead of using a standalone model; the impact of using a combination of all pairs of features instead of using all features together; the performance of the system varying attacker's capability; the most significant devices that need to be compromised while launching an attack; the resiliency of the system; and the impact of execution time for an increasing number of sensors.

SMT determines whether a first-order formula is achievable with respect to some logical theory (see also Barrett et al., Satisfiability modulo theories, In Handbook of Model Checking, pages 305-343, Springer, 2018; which is hereby incorporated by reference herein in its entirety). SMT can be leveraged and encoding can be done using boolean and real terms. Based on the satisfiability, the model produces SAT or UNSAT results. The SAT result, indicated an attack vector, the complete information about launching a successful attack on the SHS. For the UNSAT case, there is no possible attack vector under those constraints.

The formal threat modeling was implemented using the Z3 library (see also De Moura et al., Z3: An efficient smt solver, In International conference on Tools and Algorithms for the Construction and Analysis of Systems, pages 337-340, Springer, 2008; which is hereby incorporated by reference herein in its entirety). A Python application programming interface (API) of Z3 SMT solver was used. In order to determine the concave hull boundary for cluster modeling, MATLAB boundary function was used various R packages were used for evaluating clustering algorithm performance. The experiments were conducted on a Dell Precision 7920 Tower workstation with Intel Xeon Silver 4110 CPU @3.0 GHz, 32 GB memory, 4 GB NVIDIA Quadro P1000 GPU. In order to evaluate the system, a synthetic dataset was used with eight important vital features of the human body, which contains almost 17,000 samples, along with a real dataset titled The University of Queensland Vital Signs (UQVS) dataset with 209,115 samples measuring 26 vital signs.

Example 1—Assessment of Performance of ML Models

In order to assess the performance of various ML models for SHS disease classification, four different performance metrics were used: accuracy, precision, recall, and f1-score. Accuracy calculates the number of correctly identified samples of overall data samples. Precision is the measure of false-positive rate, whereas recall quantifies false-negative rate. F1-score takes both precision and recall into account by performing harmonic mean of them. FIG. 19 shows that for both synthetic and generated datasets, DT worked better than LR and NN based on accuracy, precision, recall, and f1-score.

Example 2—Assessment of Performance of ADMs

In order to assess the performance of ADMs, three different performance metrics were considered. FIG. 20 presents a comparative analysis of DBSCAN and K-means clustering based on internal cluster validation metrics including average Silhouette Coefficient Score (SCS), Davies-Bouldin Score (DBS), and Dunn's Index (DI). SCS is a measure of how similar an object is to its cluster (cohesion) compared to other clusters (separation). SCS is a measure of similarity of a cluster sample to its clusters rather than with other clusters. High value of SCS (close to +1) of a cluster specifies its likeness with its cluster where a low value (close to −1) indicates the opposite. SCS of clusters was measured by performing mean of all data points of that particular cluster, defined as the average similarity measure of each cluster with its most similar cluster, where similarity is the ratio of within-cluster distances to between-cluster distances. DBS finds the average similarity measure of each cluster compared to its most similar cluster. The clustering algorithm having a lower DBS indicates better performance. The DI value assesses compactness and clusters separation measure of the algorithm. Unlike SCS and DBS, a higher DI value denotes better performance for clustering algorithms. It is apparent from the analysis that DBSCAN outperformed k-means algorithms.

Example 3—Evaluation of System Considering a Combined Model

An IoMT-based SHS with two different types of ML models was considered for threat analysis. Based on the performance analysis, SHS was formally modeled considering DT-based DCM and DBSCAN-based ADM. The DT-based model tends to find a splitting point considering the minimum number of sensor measurements to clearly distinguish a group of vital signs from one patient status to another one. Though, DT does not consider the inter-relation between all other sensor values for a particular state, which creates a need for an ADM in addition to a DCM.

Consequently, leveraging a clustering algorithm in the SHS model can accumulate the relationship between all sensors for a particular patient state and make the system robust. NN-based DCMs might capture the inter-relationship between sensor measurements, but clustering-based approaches are required for outlier detection as NN always puts a label ignoring the fact of data being an outlier. Consideration of such a model imposes constraints on sensor measurement alteration for the adversaries. An attacker cannot alter a patient's status with the knowledge of DT-based constraints only. By compromising sensor values, the attacker could generate a sample that is satisfied by the DT-based model but labeled as an anomaly by the DBSCAN-based model as demonstrated in the case studies. Thus, the threat model can utilize an ADM along with the actual DCM for analyzing vulnerabilities of a robust healthcare system.

Example 4—Evaluation of System Considering all Pair of Features

In some embodiments of the subject invention, the threat framework does not consider the relationship among all features for the ADM. Finding a relationship among all features together results in better ADM but over-complicates the constraints increasing solver complexity and makes the threat analysis infeasible in the case of the automated real-time healthcare system. In addition, in order to draw a concave hull in the $n^{th}$ dimensional space, at least n−1 points are needed. Many clusters violate this constraint while all feature relationships are considered together. In the case of a pair of features consideration model, some abnormal data from the overall model are labeled as positive data, but no positive data was found to be anomalous. FIG. 21 shows that the pair of features consideration model can capture 95.43% and 96.64% anomalies for the synthetic and the UQVS dataset, respectively. Considering the aforementioned analysis, the pair of features consideration model can be adopted in the framework of embodiments of the subject invention.

Example 5—Performance with Respect to Attacker's Capability

Figure 8A:
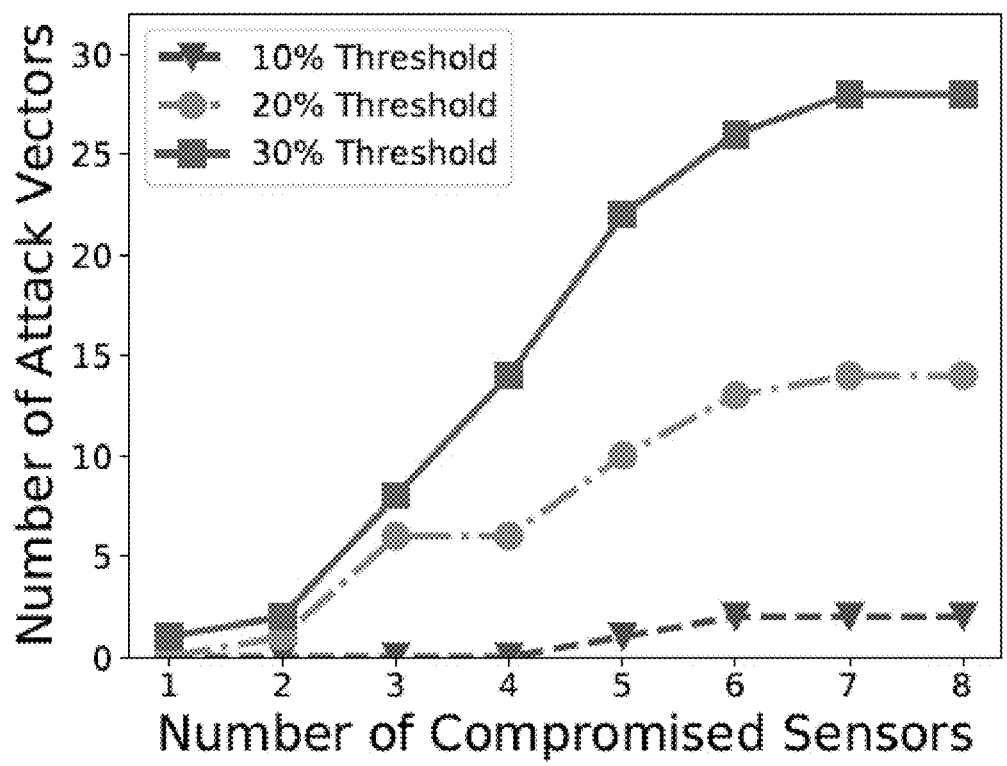
FIG. 8A shows a plot of number of attack vectors versus number of compromised sensor, showing performance of a system for threat analysis (according to an embodiment of the subject invention) with respect to an attacker's capability for a synthetic dataset. The curve with the square datapoints is for 30% threshold; the curve with the circular datapoints is for 20% threshold; and the curve with triangular datapoints is for 10% threshold.
Figure 8B:
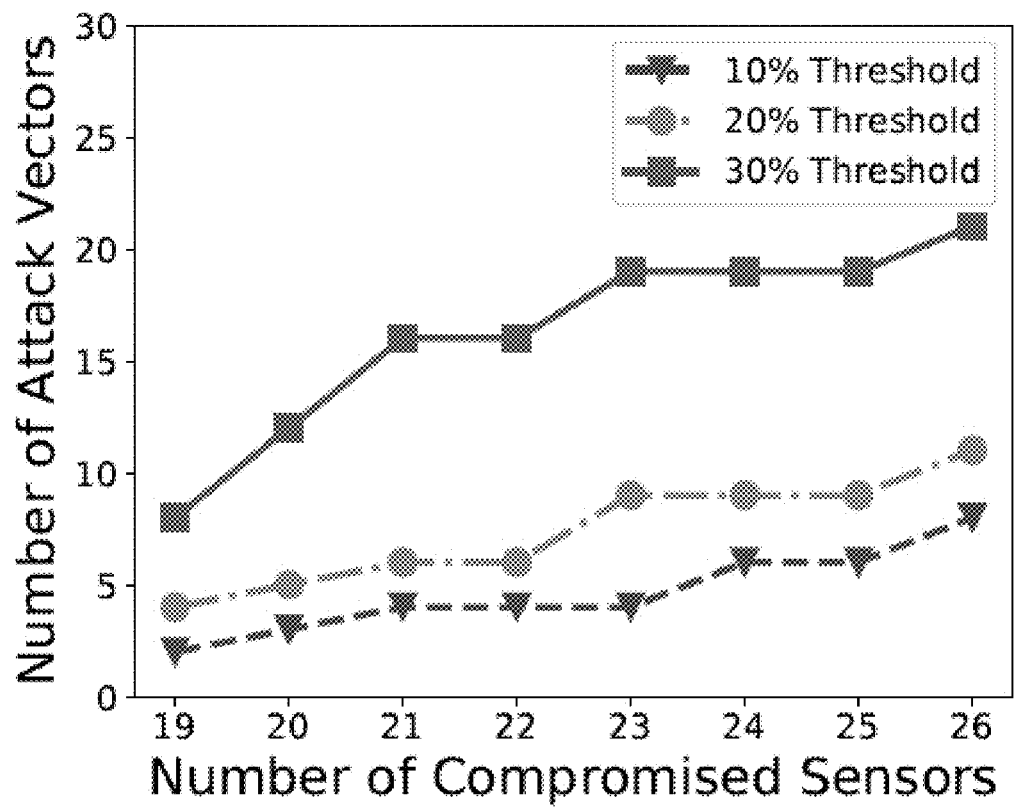
FIG. 8B shows a plot of number of attack vectors versus number of compromised sensor, showing performance of a system for threat analysis (according to an embodiment of the subject invention) with respect to an attacker's capability for The University of Queensland Vital Signs (UQVS) dataset. The curve with the square datapoints is for 30% threshold; the curve with the circular datapoints is for 20% threshold; and the curve with triangular datapoints is for 10% threshold.

The performance of the SHChecker model was evaluated by analyzing the total number of attack vectors concerning the attacker's capability. FIGS. 8A and 8B show (for the synthetic dataset and the UQVS dataset, respectively) the number of found attack vectors for the different number of compromised sensors, as well as the threshold for data injection. Referring to FIGS. 8A and 8B, the attacker is successful in finding an attack vector, even attacking only one sensor. By compromising more sensors, the attacker can achieve a maximum of three attack vectors when the injected data is bounded within a threshold of 10% of the actual sensor data. However, the model finds more attack vectors when the injection threshold is increased. The model is capable of finding 28 different attack vectors when the attacker is able to attack eight sensors, altering the measurement up to 30% of the actual value. Although SHChecker considers combination of pair of features, the attack vectors obtained using formal threat modeling conform with the actual ML models. The altered sensor measurements obtained from the attack vectors were provided as input to the DBSCAN and DT algorithms, and the output was found to be consistent with the attack goals in all cases.

Example 6—Frequency of Sensors in the Attack Vectors

Figure 9A:
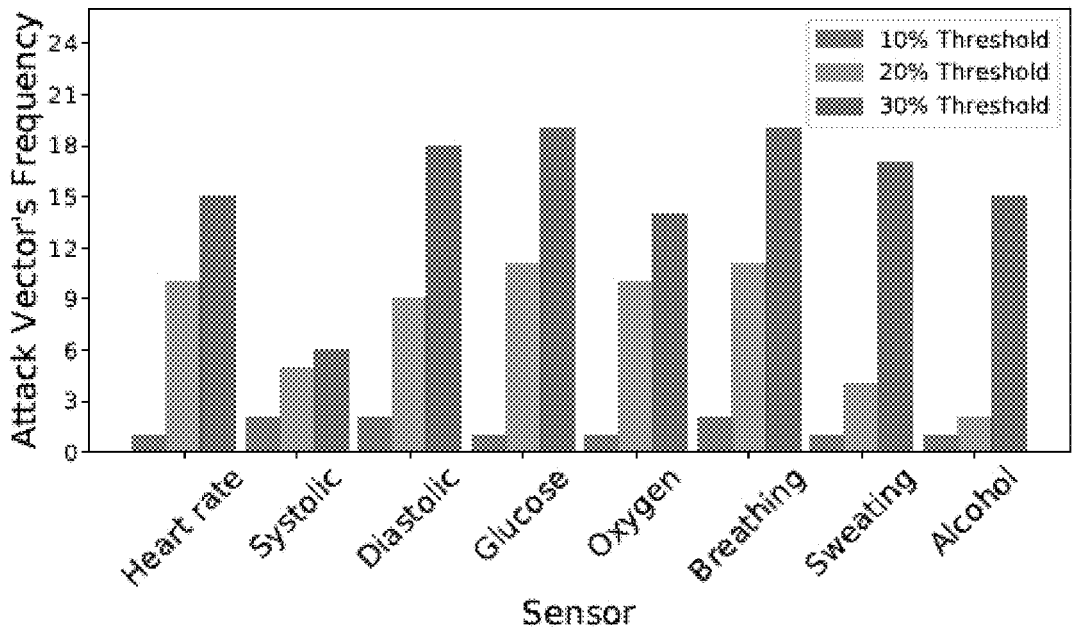
FIG. 9A shows a bar chart of attack vector frequency for several different sensors for a synthetic dataset. For each sensor, the left-most bar is for 10% threshold, the middle bar is for 20% threshold, and the right-most bar is for 30% threshold.
Figure 9B:
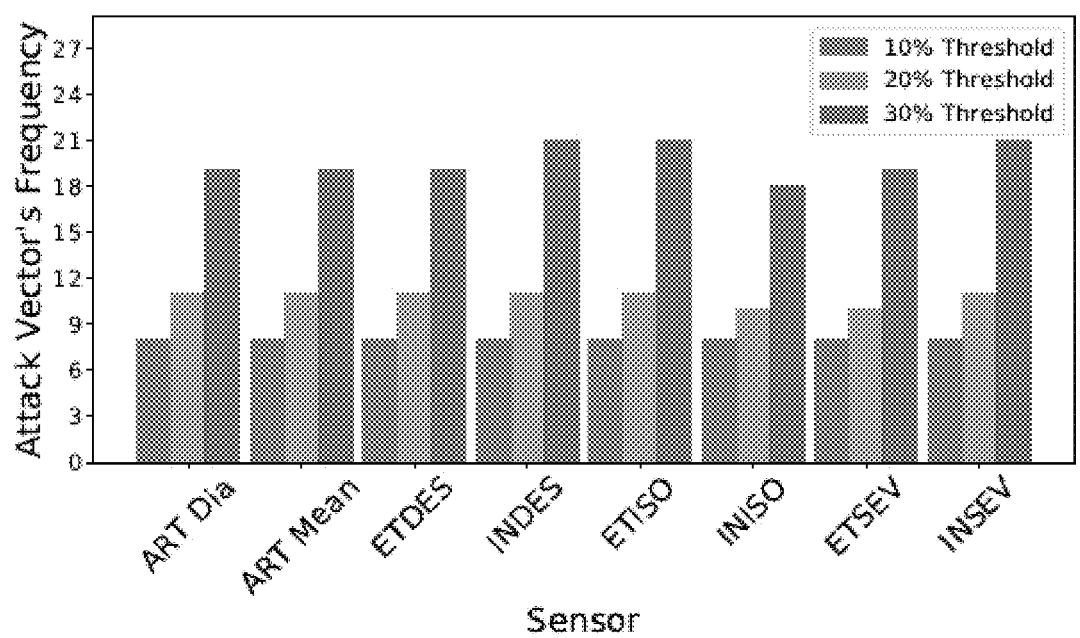
FIG. 9B shows a bar chart of attack vector frequency for several different sensors for the UQVS dataset. For each sensor, the left-most bar is for 10% threshold, the middle bar is for 20% threshold, and the right-most bar is for 30% threshold.

SHChecker framework analyzes all the attack vectors and determines the participation of the individual sensors. FIGS. 9A and 9B represent (for the synthetic dataset and the UQVS dataset, respectively) the frequency of the sensors in the attack vectors for both datasets. Referring to FIGS. 9A and 9B, all the sensors, except a few (i.e., sensor 2), participate in attack generation almost equally for 30% attack threshold. Thus, any of the sensors of the SHS can be compromised to achieve an attacker's goal. This also gives an insight on which sensors should get more attention while developing a defensive tool for the SHSs. For example, if frequency of certain sensor measurements in attack vectors is much higher than the others, the sensors associated with the measurements should get extra attention for getting secured. Thus, SHChecker can be a useful tool to provide guidelines for SHS design.

Example 7—Resiliency Analysis of the System

A system is said to be resilient to the degree to which it rapidly and effectively protects its critical capabilities from the disruption caused by adverse events and conditions. The threat model can determine the resiliency of a system for a particular attacker goal. FIG. 22 shows the resiliency table for the synthetic data, which conveys that an attacker cannot misclassify a normal patient into a high cholesterol patient if the attacker does not have access to more than two devices, which implies that the system is 2-resilient for this specific goal. An attacker with the intent to misclassify an excessive sweating state patient into a normal one or a high blood sugar patient into an abnormal oxygen level patient can become successful if the attacker has access over one particular sensor. Similarly, for the UQVS dataset, it appears that changing a patient label from normal to decrease in hemoglobin oxygen saturation (DESAT) label is 20-resilient, which signifies that an attacker cannot achieve this attack goal compromising 20 or fewer sensor measurements. Resiliency analysis capability of the framework provides a design guide specifying the relationship between the number of protected sensors with the reduction of risk.

Example 8—Scalability of SHChecker

Figure 10A:
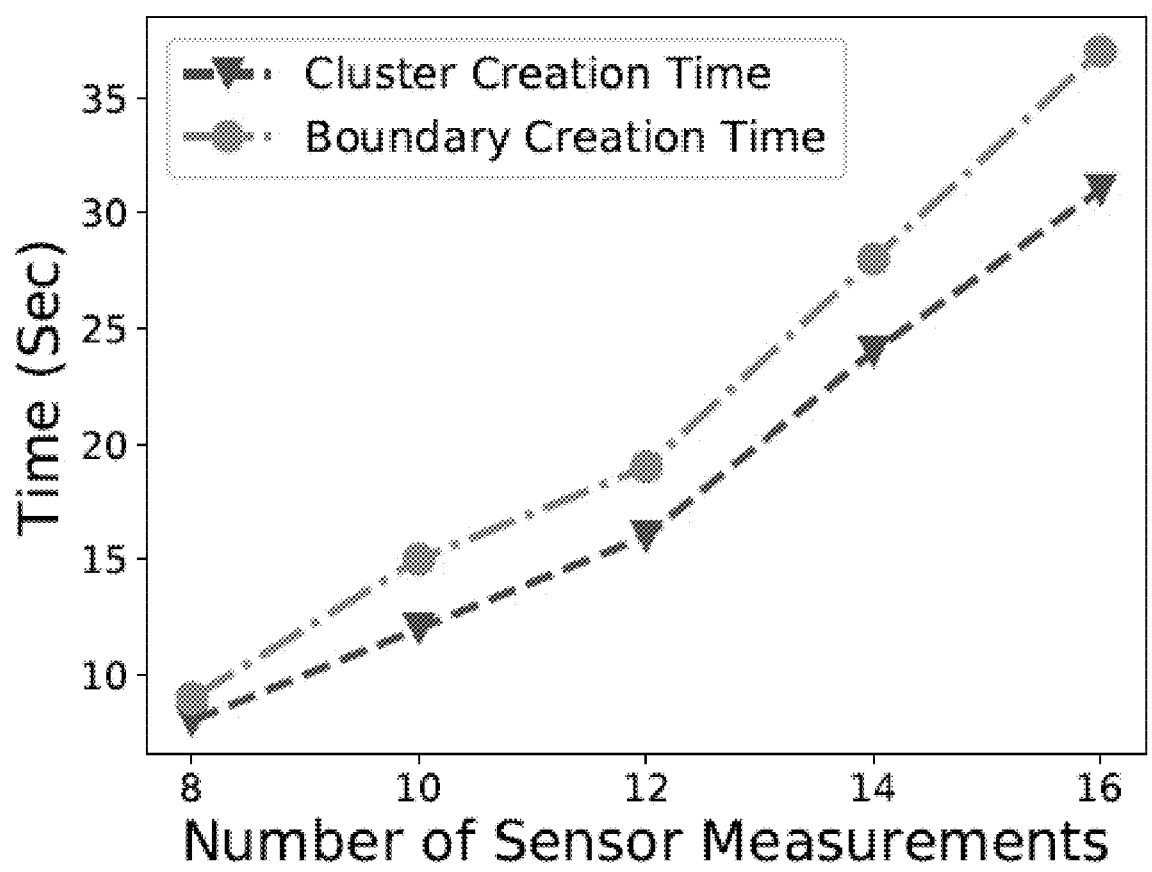
FIG. 10A shows a plot of execution time (in seconds (sec)) versus number of sensor measurements for cluster and boundary creation time, for a synthetic dataset. The curve with the circular datapoints is for boundary creation time; and the curve with the triangular datapoints is for cluster creation time.
Figure 10B:
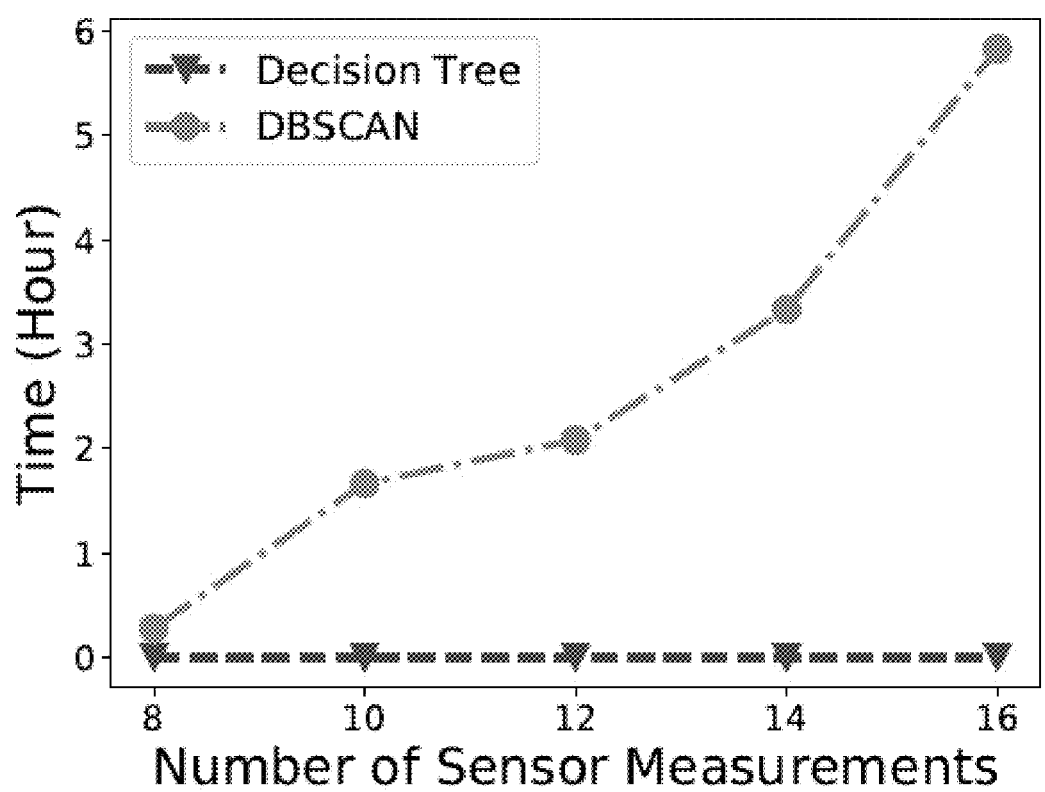
FIG. 10B shows a plot of execution time (in sec) versus number of sensor measurements for learning constraints generation, for a synthetic dataset. The curve with the circular datapoints is for DBSCAN; and the curve with the triangular datapoints is for decision tree.
Figure 10C:
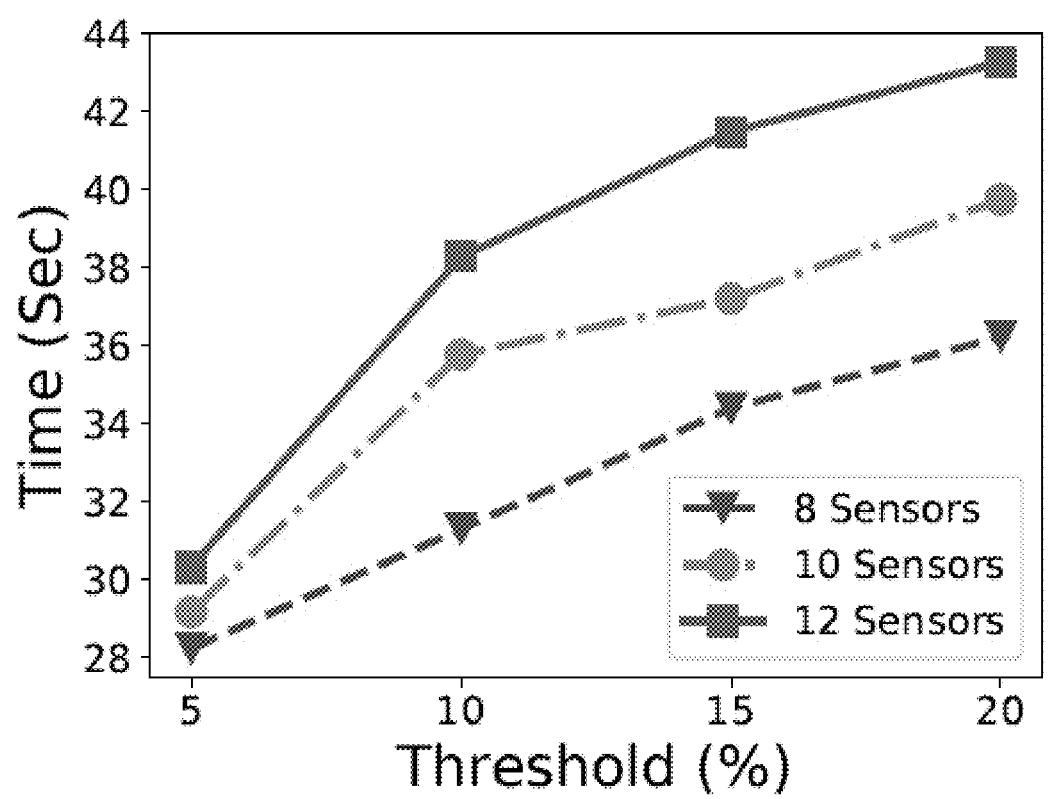
FIG. 10C shows a plot of execution time (in sec) versus threshold percentage (%) for threat analysis based on threshold for data injection, for a synthetic dataset. The curve with the square datapoints is for 12 sensors; the curve with circular datapoints is for 10 sensors; and the curve with the triangular datapoints is for 8 sensors.
Figure 10D:
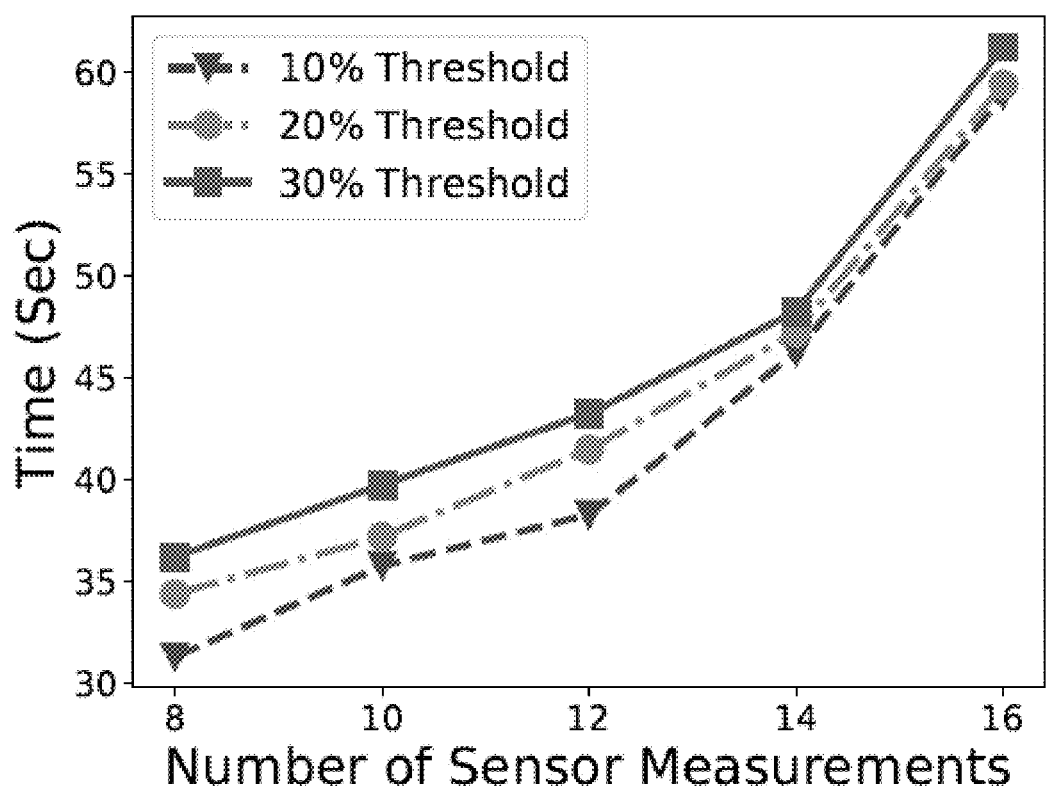
FIG. 10D shows a plot of execution time (in sec) versus number of sensor measurements for threat analysis, for a synthetic dataset. The curve with the square datapoints is for 30% threshold; the curve with circular datapoints is for 20% threshold; and the curve with the triangular datapoints is for 10% threshold.
Figure 11A:
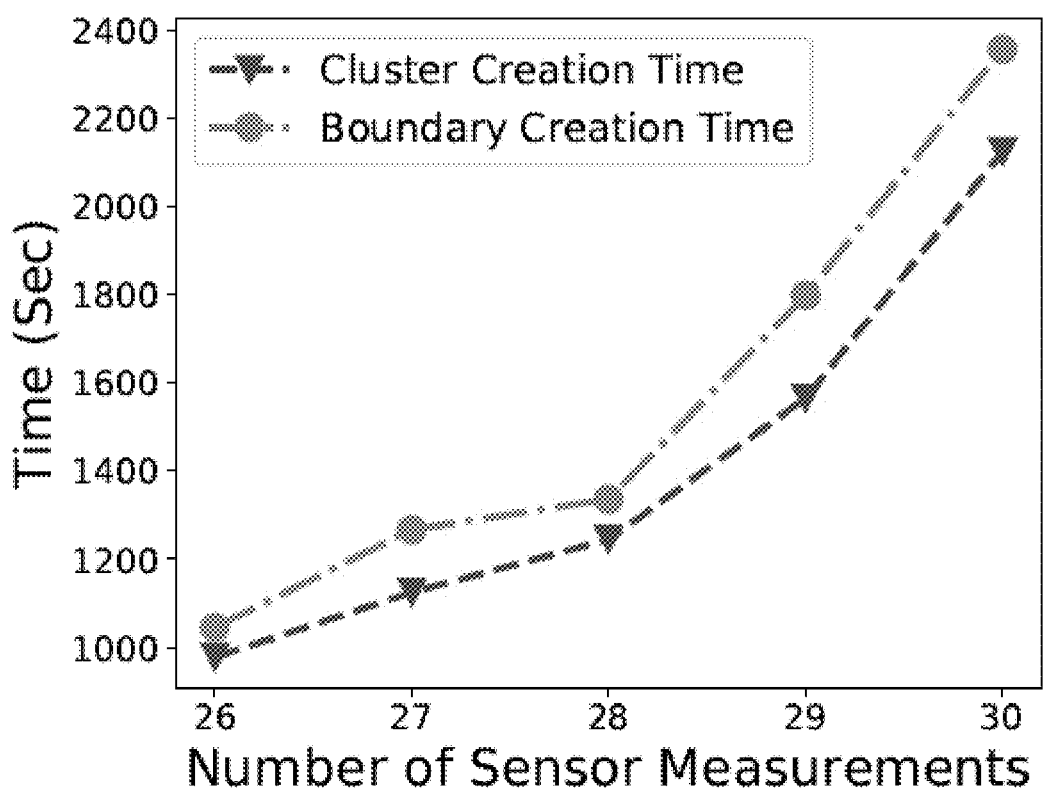
FIG. 11A shows a plot of execution time (in sec) versus number of sensor measurements for cluster and boundary creation time, for the UQVS dataset. The curve with the circular datapoints is for boundary creation time; and the curve with the triangular datapoints is for cluster creation time.
Figure 11B:
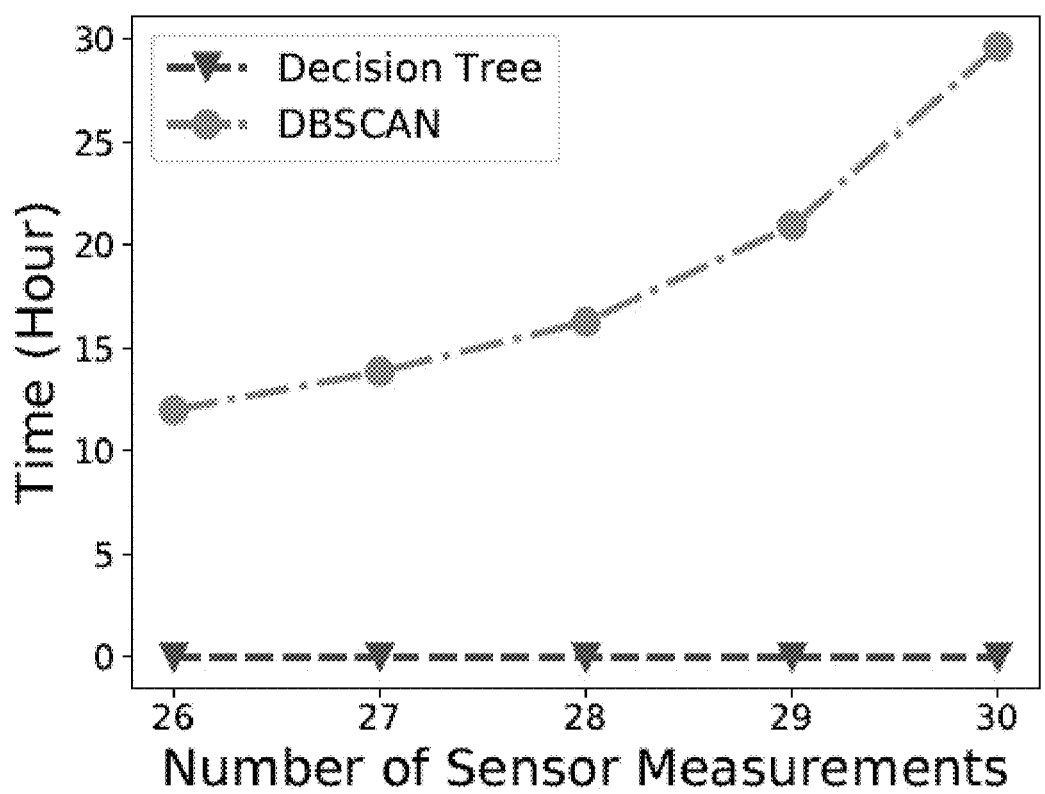
FIG. 11B shows a plot of execution time (in sec) versus number of sensor measurements for learning constraints generation, for the UQVS dataset. The curve with the circular datapoints is for DBSCAN; and the curve with the triangular datapoints is for decision tree.
Figure 11C:
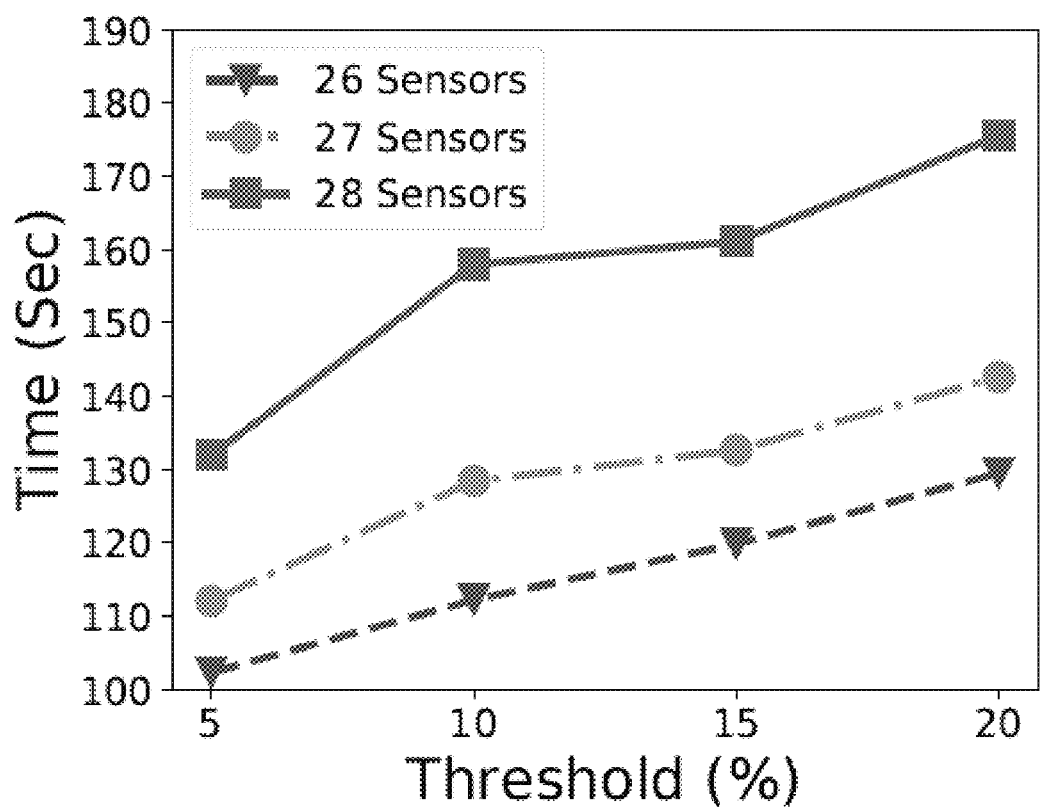
FIG. 11C shows a plot of execution time (in sec) versus threshold percentage (%) for threat analysis based on threshold for data injection, for the UQVS dataset. The curve with the square datapoints is for 28 sensors; the curve with circular datapoints is for 27 sensors; and the curve with the triangular datapoints is for 26 sensors.
Figure 11D:
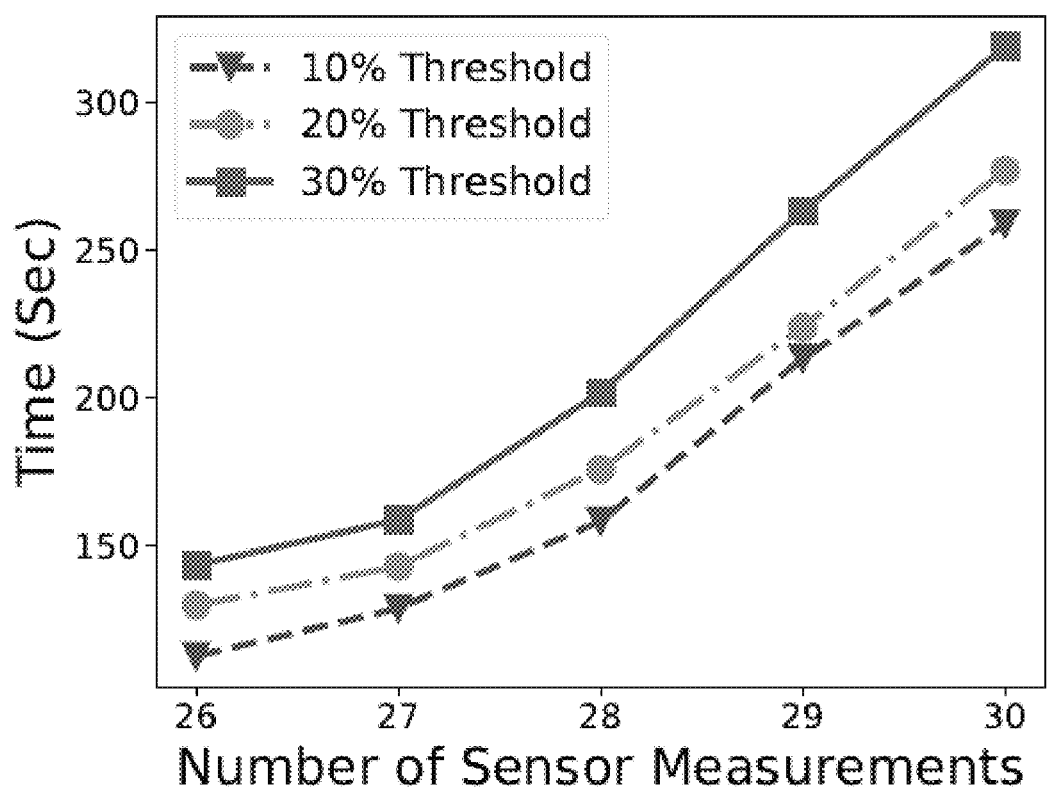
FIG. 11D shows a plot of execution time (in sec) versus number of sensor measurements for threat analysis, for the UQVS dataset. The curve with the square datapoints is for 30% threshold; the curve with circular datapoints is for 20% threshold; and the curve with the triangular datapoints is for 10% threshold.

SHChecker's scalability was evaluated by analyzing the time requirement varying size of the SHS. Scalability of the model is mainly dependent on the time required to perform threat analysis for the solver based on the attacker's capability and number of sensor measurements, and this time is the most significant determinant of attack feasibility. The number of sensors can be varied to construct the model for analyzing scalability of the system. FIGS. 10A and 11A show that execution time to create clusters from the DBSCAN constraints is less than the boundary creation time and this time increases linearly based on the number of sensor measurements. FIGS. 10B and 11B show that the construction of DBSCAN constraints requires a lot more time than that of DT clusters. However, because cluster creation, boundary creation, and constraint generation are supposed to be performed beforehand, corresponding time requirements are insignificant for attack implementation. Referring to FIGS. 10C, 11C, 10D and 11D, it is apparent that increasing the attacker's capability increases the execution time for the solver as it requires more constraints to check. The growth rate of time required for the solver performing real-time threat analysis corresponds to an exponential increment and raises scalability issues for large SHSs.

Figure 12A:
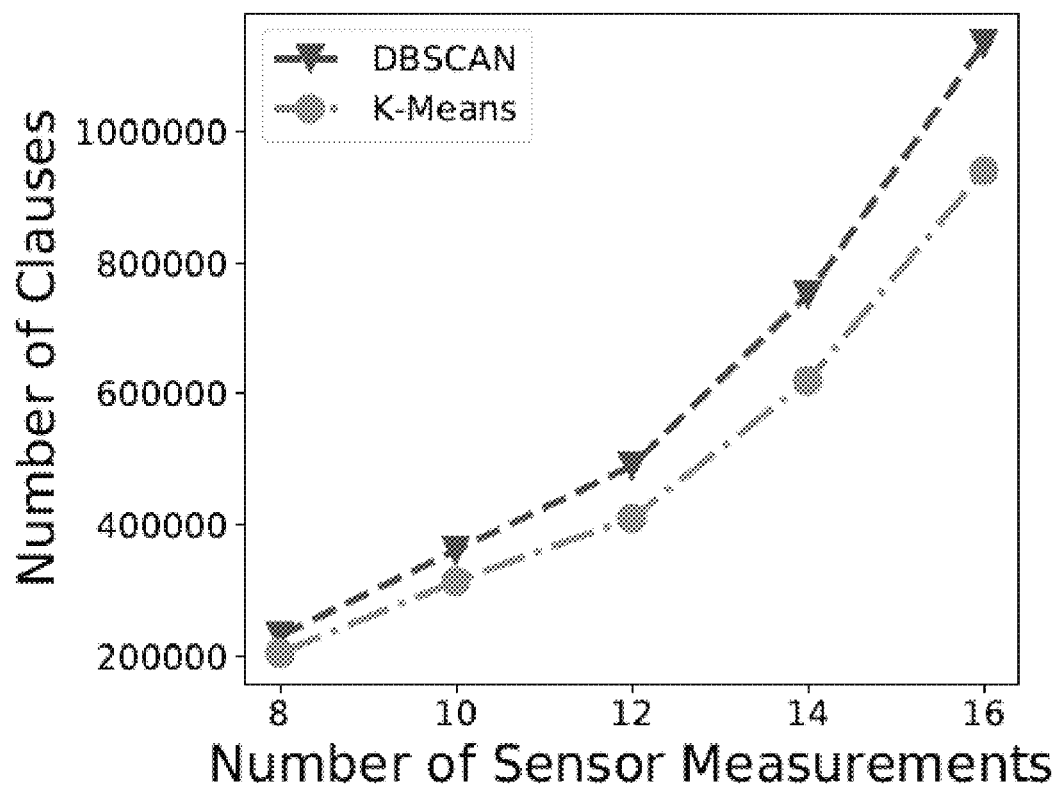
FIG. 12A shows a plot of number of clauses versus number of sensor measurements, showing a complexity analysis of anomaly detection models (ADMs) with respect to the number of measurements, for a synthetic dataset. The curve with the circular datapoints is for k-means; and the curve with the triangular datapoints is for DBSCAN.
Figure 12B:
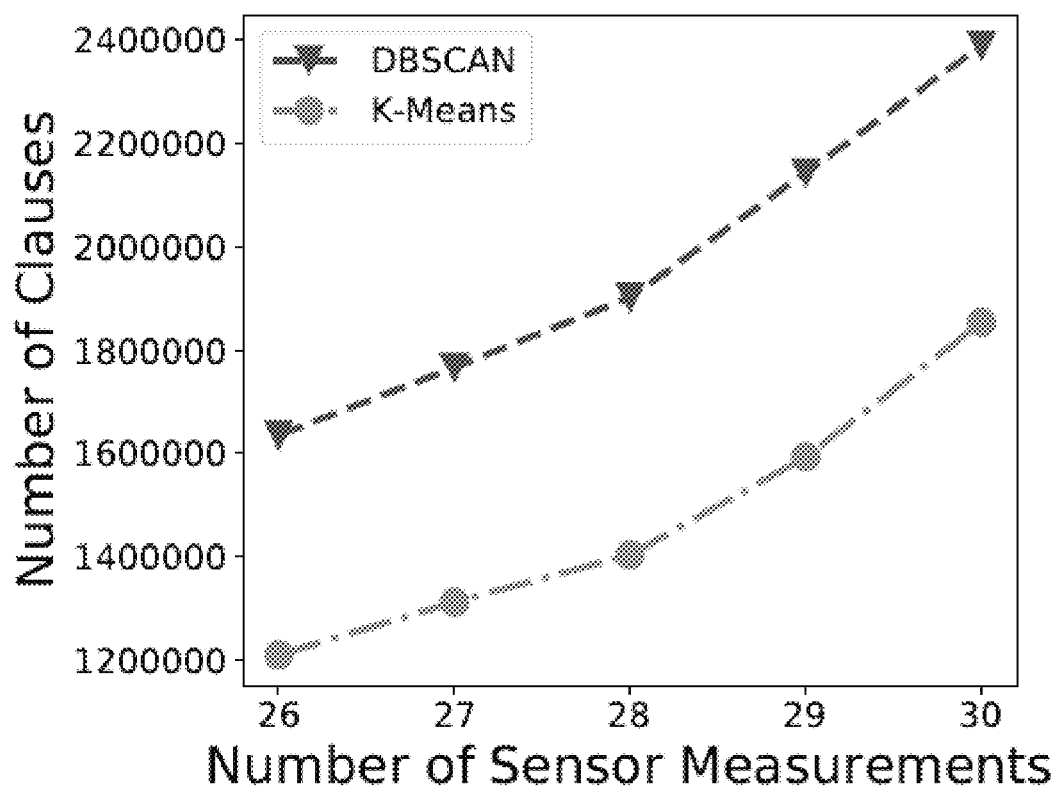
FIG. 12B shows a plot of number of clauses versus number of sensor measurements, showing a complexity analysis of anomaly detection models (ADMs) with respect to the number of measurements, for the UQVS dataset. The curve with the circular datapoints is for k-means; and the curve with the triangular datapoints is for DBSCAN.

The complexity of the solver depends on the number of clauses. The time complexity is analyzed considering DT-based DCM and DBSCAN-based ADM. FIG. 23 shows the number of clauses for various DCMs with varied number of sensor measurements. Referring to FIG. 23, it is apparent that DCMs have limited dependency on the number of sensor measurements and all three have an almost similar number of clauses. For the NN model, the number of clauses depends on the size of the architecture. A 5-layer NN with 42, 44, 48 nodes in hidden layers was used for the real dataset. For the synthetic dataset, the number of nodes in the hidden layers was 20, 12, and 8. Referring to FIGS. 12A and 12B (for the synthetic dataset and the UQVS dataset, respectively), it can be seen that ADMs are mainly responsible for solver complexity as increasing the number of features adds a large number of clauses to the solver. However, it is also clear from FIGS. 12A and 12B that both of the ADMs in consideration have given rise to a similar number of clauses. As a result, scalability analysis of other DT and DBSCAN is sufficient to understand the time requirements for other models. As the cluster creation, boundary creation, and constraint acquisition are performed beforehand, the feasibility of the attack is dependent on the time required to threat analysis only. From the experimentation, it was found that this value is slightly more than 5 minutes for 30 sensor measurements. Hence, it is possible to launch an attack for a patient monitored by an SHS whose sensor measurements are not varying drastically with time.

Example 9—Threat Analysis of Various ML Models

Figure 13A:
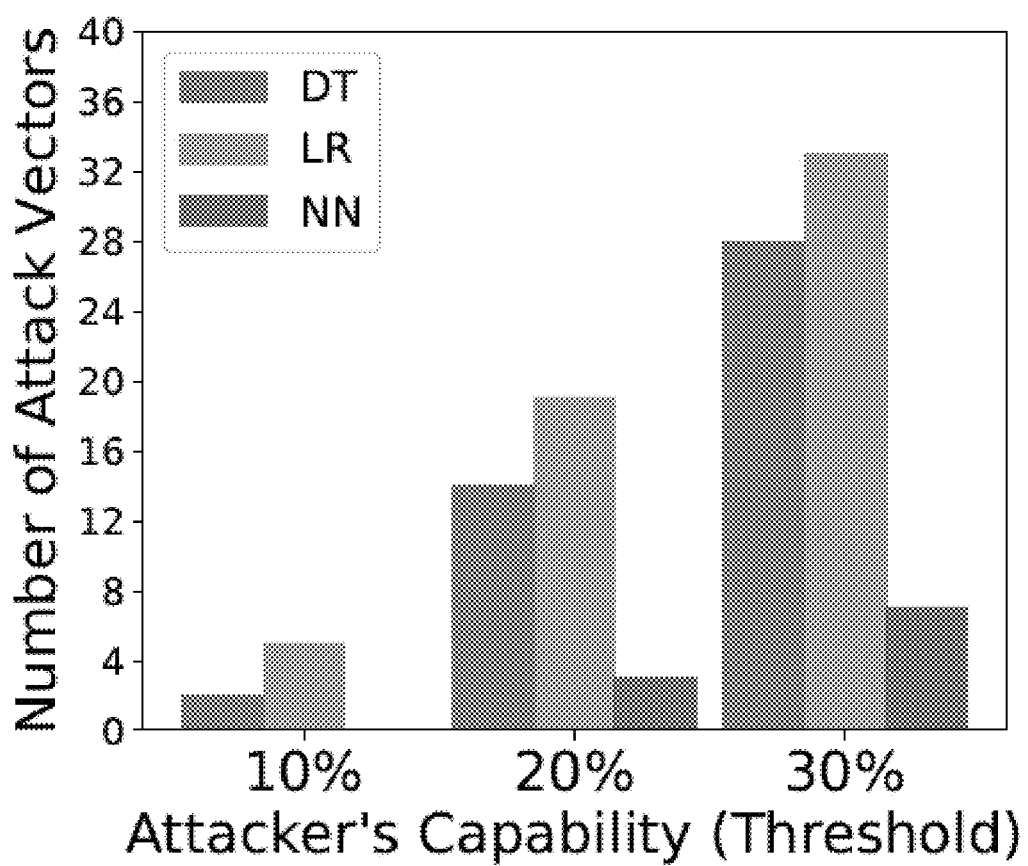
FIG. 13A shows a bar chart of number of attack vectors, showing a threat analysis of various machine learning models, for a synthetic dataset. For each threshold percentage of attacker's capability, the left-most bar is for decision tree, the middle bar is for logistic regression, and the right-most bar is for neural network.
Figure 13B:
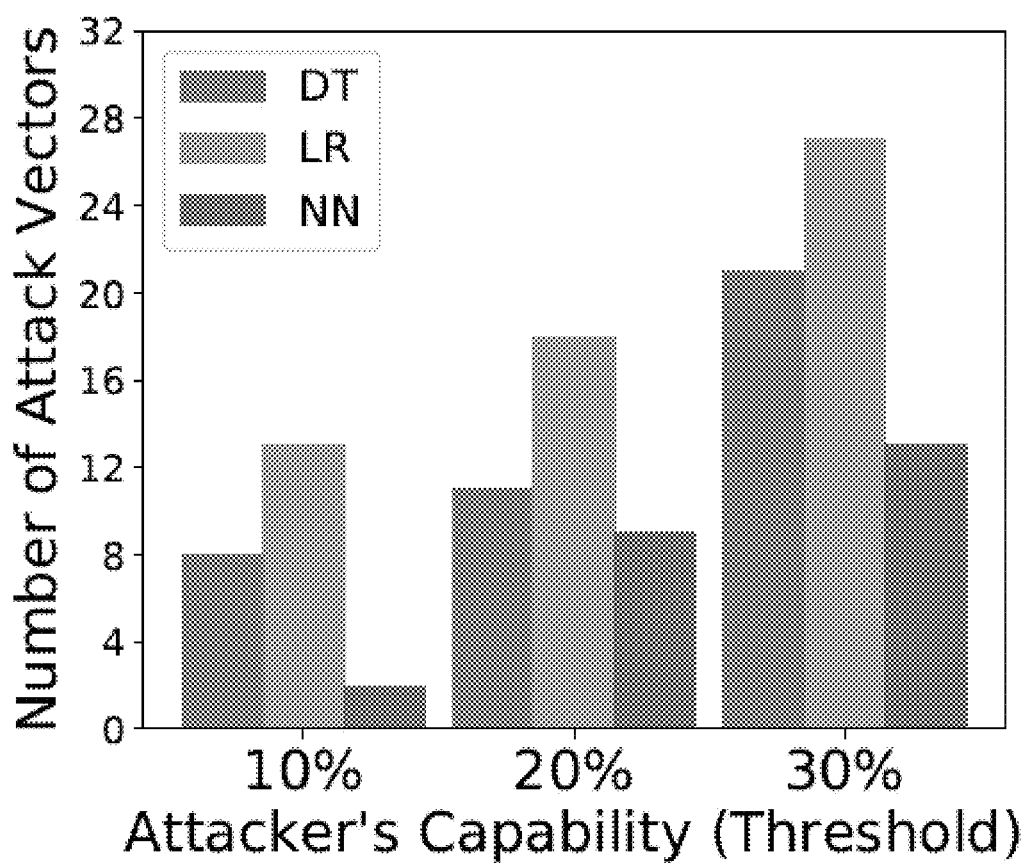
FIG. 13B shows a bar chart of number of attack vectors, showing a threat analysis of various machine learning models, for the UQVS dataset. For each threshold percentage of attacker's capability, the left-most bar is for decision tree, the middle bar is for logistic regression, and the right-most bar is for neural network.

Attack vectors of various ML models were analyzed. FIGS. 13A and 13B show (for the synthetic dataset and the UQVS dataset, respectively) the attack vector comparison varying DCMs. In this comparison, DBSCAN was considered as the ADM. The comprehensive analysis shows that logistic regression-based DCM seems to be more vulnerable than the others. Also, if the underlying DCM in use was NN instead of DT, the number of threat vectors would be fewer in number. The experimentation can be helpful while designing the decision control system. Although the NN-based model's performance based on accuracy, precision, and recall is slightly less than of the DT-based model, the DT-based model is subjected to more threats. Compromising an insignificant performance degradation can, therefore, increase the system's robustness against adversarial attacks. SHChecker can therefore be helpful in providing a design guide to SHS design by assessing the threat of various ML models.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for formal threat analysis of a smart healthcare system (SHS) that comprises an SHS database and at least one sensor collecting sensor data from at least one patient, the system comprising:
   a processor; and
   a machine-readable medium in operable communication with the processor and the SHS database, and having instructions stored thereon that, when executed by the processor, perform the following steps:
   i) training a disease classification model (DCM) using the SHS database to generate DCM output data comprising at least one label for the at least one patient;
   ii) training an anomaly detection model (ADM) using the SHS database to check consistency of the sensor data and to generate ADM output data;
   iii) running an SHS decision control model, using the DCM output data and the ADM output data as input to the SHS decision control model, to generate SHS constraints;
   iv) generating attack constraints based on a capability of a potential attacker and a goal of the potential attacker; and
   v) running a satisfiability modulo theory (SMT) solver, using the SHS constraints, the attack constraints, and the sensor data as input to the SMT solver, to determine whether the goal of the potential attacker can be attained.

2. The system according to claim 1, the instructions when executed further performing the following steps:
   vi) if the goal of the potential attacker can be attained, generating an attack vector and reporting the attack vector to a user of the system; and
   vii) if the goal of the potential attacker cannot be attained, increasing the capability of the potential attacker and running steps iv), v), vi), and vii) again.

3. The system according to claim 2, further comprising a display in operable communication with the machine-readable medium, and the reporting of the attack vector comprising displaying the attack vector on the display.

4. The system according to claim 2, the at least one sensor comprising a plurality of sensors, and
the increasing the capability of the potential attacker comprising giving the potential attacker access to at least one additional sensor than the potential attacker had access to when step iv) was most recently performed.

5. The system according to claim 2, the SMT solver first encoding the SHS constraints, the attack constraints, and the sensor data as a constraint satisfaction problem (CSP),
the SMT solver returning a result of satisfactory for the CSP if the goal of the potential attacker can be attained, and
the SMT solver returning a result of unsatisfactory for the CSP if the goal of the potential attacker cannot be attained.

6. The system according to claim 2, step vi) further comprising, after generating the attack vector and reporting the attack vector, updating the goal of the potential attacker and running steps iv), v), vi), and vii) again, and stopping once the respective attack vector has been generated and reported for all goals of a predetermined number of goals of the potential attacker.

7. The system according to claim 1, the SMT solver first encoding the SHS constraints, the attack constraints, and the sensor data as a constraint satisfaction problem (CSP),
the SMT solver returning a result of satisfactory for the CSP if the goal of the potential attacker can be attained, and
the SMT solver returning a result of unsatisfactory for the CSP if the goal of the potential attacker cannot be attained.

8. The system according to claim 1, the DCM being a decision tree (DT) algorithm, a logistic regression (LR) algorithm, or a neural network (NN) algorithm.

9. The system according to claim 1, the ADM being a density-based spatial clustering of applications with noise (DBSCAN) algorithm or a k-means algorithm.

10. The system according to claim 1, the DCM being a DT algorithm and the ADM being a DBSCAN algorithm.

11. A method for formal threat analysis of a smart healthcare system (SHS) that comprises an SHS database and at least one sensor collecting sensor data from at least one patient, the method comprising:
i) training, by a processor in operable communication with the SHS database and the at least one sensor, a disease classification model (DCM) using the SHS database to generate DCM output data comprising at least one label for the at least one patient;
ii) training, by the processor, an anomaly detection model (ADM) using the SHS database to check consistency of the sensor data and to generate ADM output data;
iii) running, by the processor, an SHS decision control model, using the DCM output data and the ADM output data as input to the SHS decision control model, to generate SHS constraints;
iv) generating, by the processor, attack constraints based on a capability of a potential attacker and a goal of the potential attacker; and
v) running, by the processor, a satisfiability modulo theory (SMT) solver, using the SHS constraints, the attack constraints, and the sensor data as input to the SMT solver, to determine whether the goal of the potential attacker can be attained.

12. The method according to claim 11, further comprising:
vi) if the goal of the potential attacker can be attained, generating an attack vector and reporting the attack vector to a user of the system; and
vii) if the goal of the potential attacker cannot be attained, increasing the capability of the potential attacker and running steps iv), v), vi), and vii) again.

13. The method according to claim 12, the reporting of the attack vector comprising displaying the attack vector on a display in operable communication with the processor.

14. The method according to claim 12, the at least one sensor comprising a plurality of sensors, and
the increasing the capability of the potential attacker comprising giving the potential attacker access to at least one additional sensor than the potential attacker had access to when step iv) was most recently performed.

15. The method according to claim 12, the SMT solver first encoding the SHS constraints, the attack constraints, and the sensor data as a constraint satisfaction problem (CSP),
the SMT solver returning a result of satisfactory for the CSP if the goal of the potential attacker can be attained, and
the SMT solver returning a result of unsatisfactory for the CSP if the goal of the potential attacker cannot be attained.

16. The method according to claim 12, step vi) further comprising, after generating the attack vector and reporting the attack vector, updating the goal of the potential attacker and running steps iv), v), vi), and vii) again, and stopping the method once the respective attack vector has been generated and reported for all goals of a predetermined number of goals of the potential attacker.

17. The method according to claim 11, the DCM being a decision tree (DT) algorithm, a logistic regression (LR) algorithm, or a neural network (NN) algorithm.

18. The method according to claim 11, the ADM being a density-based spatial clustering of applications with noise (DBSCAN) algorithm or a k-means algorithm.

19. The method according to claim 11, the DCM being a DT algorithm and the ADM being a DBSCAN algorithm.

20. A system for formal threat analysis of a smart healthcare system (SHS) that comprises an SHS database and a plurality of sensors collecting sensor data from at least one patient, the system comprising: a processor; a display; a machine-readable medium in operable communication with the processor, the display, and the SHS database, and having instructions stored thereon that, when executed by the processor, perform the following steps: i) train a disease classification model (DCM) using the SHS database to generate DCM output data comprising at least one label for the at least one patient; ii) train an anomaly detection model (ADM) using the SHS database to check consistency of the sensor data and to generate ADM output data; iii) run an SHS decision control model, using the DCM output data and the ADM output data as input to the SHS decision control model, to generate SHS constraints; iv) generate attack constraints based on a capability of a potential attacker and a goal of the potential attacker; v) run a satisfiability modulo theory (SMT) solver, using the SHS constraints, the attack constraints, and the sensor data as input to the SMT solver, to determine whether the goal of the potential attacker can be attained; vi) if the goal of the potential attacker can be attained, generating an attack vector, reporting the attack vector to a user of the system, updating the goal of the potential attacker, and running steps iv), v), vi), and vii) again, and stopping once the respective attack vector has been generated and reported for all goals of a predetermined number of goals of the potential attacker; and vii) if the goal of the potential attacker cannot be attained, increasing the capability of the potential attacker and running steps iv), v), vi), and vii) again, the reporting of the attack vector comprising displaying the attack vector on the display, the increasing the capability of the potential attacker comprising giving the potential attacker access to at least one additional sensor than the potential attacker had access to when step iv) was most recently performed, the SMT solver first encoding the SHS constraints, the attack constraints, and the sensor data as a constraint satisfaction problem (CSP), the SMT solver returning a result of satisfactory for the CSP if the goal of the potential attacker can be attained, the SMT solver returning a result of unsatisfactory for the CSP if the goal of the potential attacker cannot be attained, the DCM being a decision tree (DT) algorithm, and the ADM being a DBSCAN algorithm.

* * * * *